United States Patent [19]

Farge et al.

[11] 4,369,315
[45] Jan. 18, 1983

[54] OXACEPHALOSPORINS

[75] Inventors: Daniel Farge; Pierre Le Roy, both of Thiais; Claude Moutonnier, Le Plessis Robinson; Bernard Plau, Creteil; Jean-Francois Peyronel, Palaiseau, all of France

[73] Assignee: Rhone-Poulenc Industries, Paris, France

[21] Appl. No.: 323,113

[22] Filed: Nov. 19, 1981

[30] Foreign Application Priority Data

Nov. 20, 1080 [FR] France .............. 80 24639

[51] Int. Cl.³ .......................... C07D 498/04
[52] U.S. Cl. .......................... 544/90; 544/69
[58] Field of Search .................. 544/90, 69

[56] References Cited

U.S. PATENT DOCUMENTS 4,143,038  3/1979  Narisada et al. ............ 544/90 X
4,201,782  5/1980  Narisada et al. ............ 544/90 X
4,304,774 12/1981  Katner ...................... 544/90 X Primary Examiner—Richard Raymond Attorney, Agent, or Firm—Stevens, Davis, Miller & Mosher

[57] ABSTRACT

New oxacephalosporins of the general formula

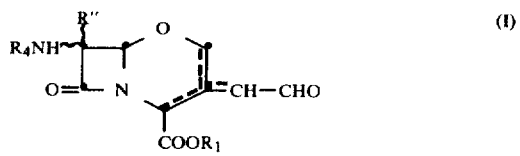

in which $R_1$ is a protective radical and (a) $R_4$ is a substituted 2-(2-aminothiazol-4-yl)-acetyl radical of which the amine group is protected, or an α-carboxyarylacetyl radical, and R" is hydrogen or methoxy in the 7α-position, or alternatively (b) $R_4$ is a protective radical and R" is hydrogen or methoxy in the 7α-position or hydrogen in the 7β-position, in the form of a bicyclooct-2-ene or bicyclooct-3-ene or a 3-oxoethylidenebicyclooctane, are useful as intermediates for the preparation of pharmaceutically active oxacephalosporins.

12 Claims, No Drawings

OXACEPHALOSPORINS

The present invention relates to new oxacephalosporins of the general formula:

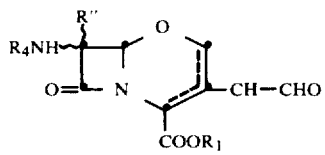

and their preparation.

The product of the general formula (I) is in the form of a bicyclooct-2-ene or bicyclooct-3-ene or a 3-oxoethylidenebicyclooctane (according to the nomenclature of Chemical Abstracts), $R_1$ is an acid-protecting radical which can easily be removed and (a) the symbol $R_4$ represents a radical of the general formula:

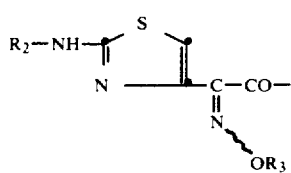

[in which $R_2$ is an amino-protecting radical and $R_3$ is a hydrogen atom, an oxime-protecting radical, an alkyl or vinyl radical or a carboxyalkyl radical represented by the general formula:

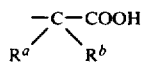

in which the radicals $R^a$ and $R^b$, which are identical or different, represent hydrogen atoms or alkyl radicals, or together form an alkylene radical containing 2 or 3 carbon atoms, and of which the acid group can be protected], or $R_4$ represents a free or protected α-carboxyarylacetyl radical in which aryl represents phenyl, free or protected p-hydroxyphenyl, or thien-2-yl or thien-3-yl, and the symbol $R''$ represents a hydrogen atom or a methoxy radical in the 7α-position, or alternatively (b) the symbol $R_4$ represents a radical which can easily be removed and the symbol $R''$ represents a hydrogen atom or a methoxy radical in the 7α-position or a hydrogen atom in the 7β-position.

It is understood that, unless otherwise mentioned, the alkyl or acyl portions or radicals which have been mentioned above (or which will be mentioned below) are linear or branched and contain 1 to 4 carbon atoms.

It is also understood that mixtures of the bicyclooct-2-ene or bicyclooct-3-ene or 3-oxoethylidenebicyclooctane isomers fall within the scope of the present invention.

Furthermore, the group $OR_3$ of the radical of the general formula (II) can be located in either the syn or anti position, and these isomers and mixtures thereof fall within the scope of the present invention.

The syn form can be represented by the general formula:

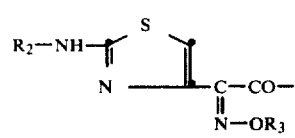

The anti form can be represented by the general formula:

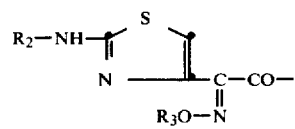

By way of example:

$R_1$ can be an acid-protecting radical chosen from amongst methoxymethyl, t-butyl, benzhydryl, benzyl, nitrobenzyl or p-methoxybenzyl;

$R_2$ can be an amino-protecting radical chosen from amongst t-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, formyl or trifluoroacetyl;

if $R_3$ is a protective radical, it can be chosen from amongst: trityl, tetrahydropyranyl, 2-methoxyprop-2-yl, alkoxycarbonyl (such as t-butoxycarbonyl) or aryloxycarbonyl (such as benzyloxycarbonyl);

if $R_3$ or if $R_4$ contains a carboxyl radical, the latter can be protected by a radical such as mentioned above for $R_1$;

if $R_4$ contains a hydroxyl group, the latter can be protected by a radical such as defined above if $R_3$ is a protective radical; or if $R_4$ is a radical which can easily be removed, it can be chosen from amongst:

(1) benzhydryl or trityl, (2) an acyl radical of the general formula:

  $R_5CO-$ (IVa)

in which $R_5$ represents:

(a) a hydrogen atom, an alkyl radical containing 1 to 7 carbon atoms, a methyl radical substituted by 1 to 3 halogen atoms, an alkenyl radical containing 3 to 7 carbon atoms or a cyanomethyl radical, (b) a phenyl radical which can be up to trisubstituted (by halogen atoms or by hydroxyl, nitro, cyano, trifluoromethyl, alkyl or alkoxy radicals), or a thien-2-yl or thien-3-yl radical, (c) a radical of the general formula:

  $R'_5YCH_2-$ (IVb)

in which $R'_5$ represents a radical such as defined under (b) and Y is a sulphur or oxygen atom, or (d) an arylalkyl radical of the general formula:

  $R''_5CH_2-$ (IVc)

in which $R''_5$ represents a phenyl radical which can be up to trisubstituted (by hydroxyl, alkyl or alkoxy radicals) or a heterocyclic radical such as thien-2-yl or thien-3-yl, furan-2-yl or furan-3-yl or tetrazol-1-yl, (3) a radical of the general formula:

 (IVd)

in which R₆ is an unsubstituted branched alkyl radical, a linear or branched alkyl radical carrying one or more substituents such as halogen atoms or cyano radicals, phenyl radicals or phenyl radicals substituted by one or more halogen atoms or alkyl, alkoxy, nitro or phenyl radicals, a 2-trimethylsilylethyl radical, a vinyl or allyl radical or a quinolyl radical, (4) a radical of the general formula:

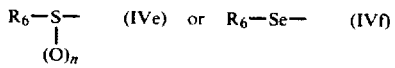

in which formulae the radical R₆ is an alkyl or phenyl radical or a phenyl radical substituted by one or more halogen atoms or nitro or alkyl radicals, and n is equal to 0 or 1, or (5) a bis-(4-nitrobenzyl)-phosphoryl radical, or alternatively (6) R₄NH— can be replaced by an alkylaminomethyleneamino radical or by a radical of the general formula:

 (IVg)

in which Ar is a phenyl group optionally substituted by one or more radicals such as alkoxy, nitro, alkyl or hydroxyl.

The following radicals may be mentioned as examples of radicals R₄ which can be used: formyl, acetyl, chloroacetyl, trichloroacetyl, phenylacetyl, phenoxyacetyl, benzoyl, t-butoxycarbonyl, 2-chloro-1,1-dimethylethoxycarbonyl, 2,2,2-trichloroethoxycarbonyl, 2,2,2-trichloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio, p-nitrophenylthio and bis-(4-nitrobenzyl)-phosphoryl.

The following may be mentioned as examples of methyleneamino radicals defined above under (6): dimethylaminomethyleneamino, 3,4-dimethoxybenzylideneamino, 4-nitrobenzylideneamino and 3,5-di-t-butyl-4-hydroxybenzylideneamino.

According to the invention, the products of the general formula (I) can be obtained by hydrolysing the enamine (or a mixture of isomeric enamines) of the general formula:

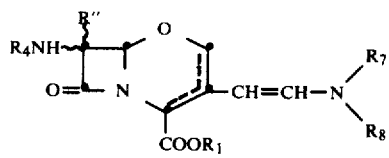 (V)

in which, R″, R₁ and R₄ being defined as above (it being understood that, if necessary, the carboxy radical contained in R₄ is protected), the product is in the form of a bicyclooct-2-ene or bicyclooct-3-ene, the substituent on the carbon atom in the 3-position of the bicyclooctene exhibits cis/trans stereoisomerism (hereafter designated respectively by Z or E) and R₇ and R₈, which are identical or different, represent alkyl radicals (optionally substituted by an alkoxy or dialkylamino radical) or phenyl radicals, or together form, with the nitrogen atom to which they are attached, a 5- or 6-membered saturated heterocyclic ring optionally containing another hetero-atom chosen from amongst nitrogen, oxygen or sulphur, and optionally substituted by alkyl radical.

The reaction is generally carried out in an organic acid (e.g. formic acid or acetic acid) or a mineral acid (e.g. hydrochloric acid or sulphuric acid), in the presence or absence of a solvent, in an aqueous or organic medium, at a temperature between −20° C. and the reflux temperature of the reaction mixture. If the reaction is carried out in an organic medium, the hydrolysis is performed by the addition of water to the reaction mixture, followed, if appropriate, by treatment with an inorganic base (e.g. an alkali metal bicarbonate) or an organic base (e.g. a tertiary amine or pyridine).

If the reaction is carried out in the presence of a solvent, it is not necessary for the solvent to be miscible with the acid aqueous phase. In that case, contact is effected by vigorous stirring.

Chlorinated solvents, ethyl acetate, tetrahydrofuran, acetonitrile, dimethylformamide and alcohols may be mentioned amongst the solvents which can be used. It is not absolutely necessary to have purified the intermediate of the general formula (V) in order to carry out this reaction.

If it is desired to obtain an aldehyde of the general formula (I) in which R₄ contains a free acid group, it is necessary to carry out the reaction starting from an enamine in which R₁ and the protective group of the acid group of R₄ are different and can be removed selectively.

The removal of the protective radical is carried out under the conditions described below.

The products of the general formula (V) can be obtained by reacting a product, optionally prepared in situ, of the general formula:

 (VI)

[in which R₇ and R₈ are defined as above and R₉ and R₁₀, which are identical or different, either represent groups of the general formula:

 (VII)

in which X₂ represents an oxygen atom and R₁₁ represents an alkyl or phenyl radical, or represent in one case a radical of the general formula (VII) (in which X₂ represents an oxygen or sulphur atom and R₁₁ is alkyl or phenyl) and in the other case an amino radical of the general formula:

in which R₁₂ and R₁₃ are defined in the same way as R₇ and R₈), or R₉ and R₁₀ each represent a radical of the general formula (VIII)] with an oxacephalosporin derivative of the general formula:

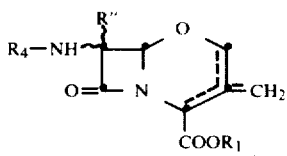

in which, R", R₁ and R₄ being defined as above in the general formula (V), the product is in the form of a 3-methyl-bicyclooct-2-ene or -bicyclooct-3-ene or a 3-methylenebicyclooctane.

If a product of the general formula (VI) in which the radical (VIII) is different from —NR₇R₈ is chosen, it is preferable to choose this product so that the amine HNR₁₂R₁₃ is more volatile than HNR₇R₈.

The reaction is generally carried out in an organic solvent such as an amide (e.g. dimethylformamide, dimethylacetamide or hexamethylphosphorotriamide), a nitrile (e.g. acetonitrile), an ester (e.g. ethyl acetate), an ether (e.g. dioxane) or a chlorinated solvent (e.g. 1,2-dichloroethane), or in a mixture of these solvents, at a temperature between 20° C. and the reflux temperature of the reaction mixture.

It is understood that if R₄ represents a radical of the general formula (II) in which R₃ represents a hydrogen atom, it is preferable for the oxime to be protected under the conditions described above.

It is also understood that if R₄ contains a hydroxyl substituent, it is preferable to protect the latter.

The protection of the radicals is effected under the conditions described above.

The removal of the protective radicals is carried out under the conditions described below for the products of the general formula (XIV).

The products of the general formula (VI) can be prepared in accordance with the methods described by H. BREDERECK et al., Chem. Ber. 101, 41 (1968), Chem. Ber. 101, 3,058 (1968) and Chem. Ber. 106, 3,725 (1973).

The oxacephalosporin derivatives of the general formula (IX) in which R₄ represents a radical of the general formula (II) or an α-carboxyarylacetyl radical of which the acid groups are protected can be prepared from the products of the general formula:

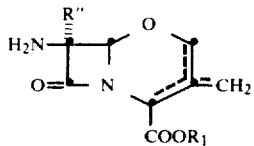

in which R₁ is defined as above and R" represents a hydrogen atom or a methoxy radical in the 7α-position, by reaction with an acid of the general formula:

R₄OH (XI)

in which R₄ is defined as above, or with a reactive derivative of this acid, under the conditions described below under II. for the preparation of the products of the general formula (XII).

The oxacephalosporins of the general formulae (IX) and (X) can be prepared in accordance with or by analogy with the methods described in the literature, e.g.:

if R" represents a hydrogen atom: in accordance with the methods described by C. L. BRANCH et al., J.C.S. Perkin I, 2,268 (1979), in German patent application No. 2,806,457, in U.S. Pat. No. 4,108,992 and in German patent application 2,355,209, followed, if appropriate, by the introduction of the radical R₄ [if it is desired to obtain a product of the general formula (IX)] by analogy with the methods employed in cephalosporin chemistry and e.g.:

if R₄ is a formyl radical: according to J. C. SHEEHAN et al., J. Amer. Chem. Soc. 80 1,154 (1958), if R₄ is acetyl, chloroacetyl, trichloroacetyl, phenylacetyl, phenoxyacetyl or benzoyl: according to E. H. FLYNN, Cephalosporins and Penicillins, Ac. Press (1972), if R₄ is a t-butoxycarbonyl radical: according to L. MORODER et al., Hoppe Seyler's Z. Physiol. Chem. 357 1,651 (1976), if R₄ is 2,2,2-trichloro-1,1-dimethylethoxycarbonyl: according to J. UGI et al., Agnew. Chem.Int. Ed. Engl. 17(5) 361 (1978), if R₄ is 2,2,2-trichloroethoxycarbonyl, 2-chloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl: by reaction with a chloroformate in an aqueous-organic medium, in the presence of an alkali metal bicarbonate, or according to Belgian Pat. No. 788,885, if R₄ is diphenylmethoxycarbonyl: by reaction with the corresponding azidoformate in an aqueous-organic medium, in the presence of an alkali metal bicarbonate, if R₄ is 2-(biphenyl-4-yl)-isopropoxycarbonyl: by analogy with the method described in Helv. Chim. Acta, 51, 924 (1968), if R₄ is quinol-8-yl-oxycarbonyl or allyloxycarbonyl: by reaction with the corresponding carbonate in a basic aqueous-organic medium, if R₄ is o-nitrophenylthio or p-nitrophenylthio: by analogy with the method described by T. KOBAYASHI et al., Chem. Pharm. Bull. 27(11) 2,718 (1979), if R₄NH is replaced by dimethylaminomethyleneamino: by analogy with the method described by J. F. FITT, J. Org. Chem. 42(15), 2,639 (1977), if R₄NH is replaced by 4-nitrobenzylideneamino or 3,4-dimethoxybenzylideneamino: in accordance with the method described by R. A. FIRESTONE, Tetrahedron Lett., 375 (1972), if R₄NH is replaced by 3,5-di-t-butyl-4-hydroxybenzylideneamino: in accordance with the method described by H. YANAGISAWA et al., Tetrahedron Lett., 2,705 (1975), or if R₄ is bis-(4-nitrobenzyl)-phosphoryl: in accordance with the method described in Japanese patent application 77/125,185, or if R" represents a methoxy radical: by analogy with the methods described below for the preparation of the products of the general formula (XXI) or (XXIIa) or according to German patent application 2,806,457, and then, if it is desired to obtain a product of the general formula (IX), introduction of the radical R₄ by analogy with the methods mentioned above.

The products of the general formula (X) can be prepared in accordance with the method described in Belgian Pat. No. 850,662 or by applying the method described in Belgian Pat. No. 877,884 if R₄ is a radical of the general formula (II) in which $R_3$ is hydrogen or alkyl.

The products of the general formula (X) can be prepared in accordance with the method described in Belgian Pat. No. 869,079 if $R_4$ is a radical of the general formula (II) in which $R_3$ is vinyl.

The products of the general formula (X) can be prepared in accordance with the methods described in Belgian Patents 864,810, 865,298, 876,541 and 876,542 if $R_4$ is a radical of the general formula (II) in which $R_3$ is a substituent of the general formula (III).

If $R_4$ is an α-carboxyarylacetyl radical, the products of the general formula (X) can be prepared in accordance with the following methods:

if the aryl group represents a p-hydroxyphenyl group: in accordance with the method described in Japanese patent application Ser. No. 79/106,447 or in Belgian Pat. No. 852,912;

if the aryl group represents a thien-2-yl group: according to D. IVANOV and N. MAREKOV, Compt. Rend. Acad. Bulgare Sci., 8(11), 29 (1955); or if the aryl group represents a thein-3-yl group: according to British Pat. No. 1,125,557.

The new products of the general formula (I) are useful as intermediates for the preparation of thiovinyloxacephalosporins of the general formula:

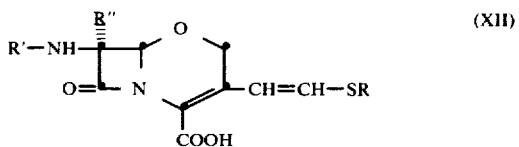

(XII)

in which the symbol R is chosen from amongst the following meanings:

(1) optionally N-oxidised pyrid-2-yl, pyrid-3-yl or pyrid-4-yl,
(2) pyrimidin-2-yl,
(3) 6-methylpyridazin-3-yl-1-oxide,
(4) 5,6-dioxo-1,4,5,6-tetrahydro-1,2,4-triazin-3-yl substituted in the 4-position by
   (a) an alkyl radical containing 1 or 2 carbon atoms, which is optionally substituted by an alkoxy, alkylthio or formyl radical,
   (b) an allyl, 2,3-dihydroxypropyl, 1,3-dihydroxyprop-2-yl or 2-formyl-2-hydroxyethyl radical, or
   (c) an alkyl radical containing 2 or 3 carbon atoms, which is substituted by hydroxyl, carbamoyloxy, acyloxy or acylamino (the acyl portions of which are unsubstituted or substituted by amino), alkylsulphonylamino, ureido, alkylureido or dialkylureido,
(5) 5,6-dioxo-1,4,5,6-tetrahydro-1,2,4-triazin-3-yl substituted in the 1-position, or 5,6-dioxo-1,2,5,6-tetrahydro-1,2,4-triazin-3-yl substituted in the 2-position, by an alkyl radical containing 1 or 2 carbon atoms, which is optionally substituted by a formyl radical,
(6) 2-alkyl-2,5-dihydro-5-oxo-1,2,4-triazin-3-yl optionally substituted in the 6-position by an alkyl or alkoxy radical, the alkyl portions and radicals of which contain 1 or 2 carbon atoms,
(7) 1-amino-1,2-dihydro-2-oxopyrimidin-4-yl,
(8) 1,3,4-thiadiazol-5-yl substituted by alkyl, dialkylaminoalkyl or acylaminoalkyl,
(9) tetrazol-5-yl substituted in the 1-position by
   (a) an alkyl radical containing 1 or 2 carbon atoms, which is optionally substituted by a formyl radical,
   (b) an alkyl radical containing 2 or 3 carbon atoms, which is substituted by hydroxyl, acylamino or dialkylamino, or
   (c) a 2,3-dihydroxypropyl or 1,3-dihydroxyprop-2-yl radical, or
(10)
   (a) 1-alkyl-1,2,4-triazol-5-yl optionally substituted in the 3-position by an alkoxycarbonyl radical, the alkyl and alkoxy radicals of which contain 1 or 2 carbon atoms, or
   (b) 1-alkyl-1,3,4-triazol-5-yl, the symbol $R'$ represents a radical of the general formula (II) in which $R_2$ is a hydrogen atom and $R_3$ is a hydrogen atom, an alkyl or vinyl radical or a carboxyalkyl radical of the general formula (III) in which $R^a$ and $R^b$ are defined as above, or $R'$ represents an α-carboxyarylacetyl radical in which aryl represents phenyl, p-hydroxyphenyl or thien-2-yl or thien-3-yl, and the symbol $R''$ is a hydrogen atom or a methoxy radical in the 7α-position.

It is understood that the substituent in the 3-position of the products of the general formula (XII) can be in the E or Z form.

I. The 3-thiovinyloxacephalosporins of the general formula (XII) can be prepared by the following procedure:

(A) An activated derivative of the acids $R'_{14}SO_3H$ or $R''_{14}COOH$, of the type:

| | | |
|---|---|---|
| $(R'_{14}SO_2)_2O$ | (a) | |
| $R'_{14}SO_2Hal$ | (b) | |
| | | (XIII) |
| $(R''_{14}CO)_2O$ | (c) | |
| $R''_{14}COHal$ | (d) | |

[in which formulae $R'_{14}$ is an alkyl, trifluoromethyl or trichloromethyl radical or a phenyl radical optionally substituted by a halogen atom or by an alkyl or nitro radical, and $R''_{14}$ is defined in the same way as $R'_{14}$ or represents an acylmethyl, 2-acylethyl, 2-acylpropyl, alkoxycarbonylmethyl, 2-alkoxycarbonylethyl or 2-alkoxycarbonylpropyl radical, and Hal represents a halogen atom], or a halogenating agent, is reacted with a product of the general formula (I), or with a mixture of its isomers, and then the protective radicals are removed, if appropriate, in order to obtain a product of the general formula:

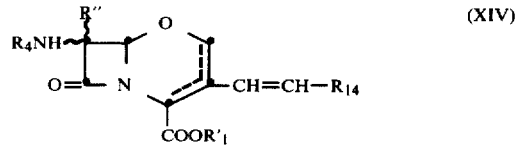

(XIV)

which is in the form of a bicyclooct-2-ene or bicyclooct-3-ene and in which (a₁) the symbol $R'_1$ is a hydrogen atom or a protective radical such as defined above for $R_1$, the symbol $R_4$ is defined as above for the products of the general formula (I) under (a) or represents a radical of the general formula (II) in which the radical $R_2$ represents a hydrogen atom, and the symbol $R''$ is defined as above under (a), or alternatively (b₁) the symbol $R'_1$ is defined in the same way as $R_1$ above and the symbols $R_4$ and $R''$ are defined as above under (b), and the symbol $R_{14}$ is a radical of the general formula:

$$R'_{14}SO_2O— \quad (XVa)$$

$$R''_{14}COO— \quad (XVb)$$

in which formulae $R'_{14}$ and $R''_{14}$ are defined as above, or $R_{14}$ is a halogen atom chosen from amongst chlorine, bromine and iodine, and of which the substituent in the 3-position of the bicyclooctene exhibits E/Z stereoisomerism.

If it is desired to use a product of the general formula (I) in which $R_4$ is a radical of the general formula (II) of which the radical $R_3$ is a hydrogen atom, it is necessary to protect the oxime beforehand.

If it is desired to use an aldehyde of the general formula (I) in which $R_4$ contains a carboxyl group, this radical can be free or protected if an activated derivative of the acids $R'_{14}SO_3H$ or $R''_{14}COOH$ is reacted; on the other hand, it is necessary to protect it beforehand if a halogenating agent is reacted.

If it is desired to use an aldehyde in which the radical $R_4$ is α-carboxy-(p-hydroxyphenyl)-acetyl, it is necessary to protect the hydroxyl radical.

The protection of the radicals is effected under the conditions described above.

The reaction is generally carried out in the presence of a tertiary base of the general formula

$$X_1—N\begin{matrix}Y_1\\Z_1\end{matrix} \quad (XVI)$$

in which $X_1$, $Y_1$ and $Z_1$ represent alkyl or phenyl radicals, or, if appropriate, two of them form a ring with the nitrogen atom to which they are attached, e.g. triethylamine or N,N-dimethylaniline, in a chlorinated organic solvent (e.g. methylene chloride), in an ester (ethyl acetate), in an ether (e.g. dioxane or tetrahydrofuran), in an amide (e.g. dimethylacetamide or dimethylformamide), in acetonitrile or N-methylpyrrolidone or in a mixture of these solvents, or directly in a basic solvent such as pyridine, or alternatively, if $R_{14}$ is other than a halogen atom, the reaction can be carried out in an aqueous-organic medium, in the presence of an alkaline condensation agent (e.g. an alkali metal bicarbonate, sodium hydroxide or potassium hydroxide), at a temperature between −78° C. and the reflux temperature of the reaction mixture.

If appropriate, the reaction is carried out under nitrogen.

It is not absolutely necessary to have purified the product of the general formula (I) in order to use it in this reaction.

If it is desired to prepare a product of the general formula (XIV) in which $R_{14}$ is a halogen atom, the halogenating agent can be chosen from amongst halogen derivatives of phosphorus, in particular:

triaryl phosphite/halogen addition compounds, or phosphorus trichloride, phosphorus oxychloride, phosphorus pentachloride, dichlorotriphenylphosphorane or catechyltrichlorophosphorane if $R_{14}$ is a chlorine atom, or phosphorus tribromide, phosphorus oxybromide, phosphorus pentabromide or catechyltribromophosphorane if $R_{14}$ is a bromine atom.

Catechyltrichlorophosphorane (or catechyltribromophosphorane), which can be prepared in situ, can be obtained in accordance with the method described by H. GROSS and U. KARSCH, J. Prakt. Chem., 29, 315 (1965).

The triaryl phosphite/halogen addition compounds, which can be prepared in situ, are described by H. N. RYDON and B. L. TONGE, J. Chem. Soc., 3,043 (1956), by J. MICHALSKI et al., J. Org. Chem., 45, 3,122 (1980), or in Belgian Patent 881,424, and can be prepared in accordance with the methods mentioned in these documents.

The preparation of the halogen derivatives of the general formula (XIV) is carried out in an anhydrous medium.

If it is desired to prepare a product of the general formula (XIV) in which $R_{14}$ is a chlorine or bromine atom, depending on the operating conditions, it is possible to isolate the dihalogen intermediate of the general formula:

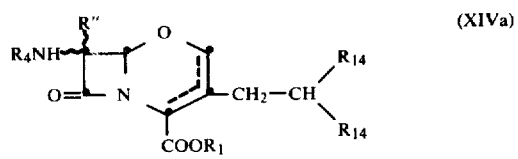

(XIVa)

[in which R″, $R_4$ and $R_1$ are defined as for the product of the general formula (I) used, and $R_{14}$ is defined as above, the product exhibiting the same isomerism as the product of the general formula (XIV)], which is then dehydrohalogenated.

If it is desired to isolate the dihalogen intermediate, the reaction is carried out with a halogenating agent, in an organic solvent such as a chlorinated solvent (e.g. methylene chloride, chloroform, carbon tetrachloride or 1,2-dichloroethane), an ether (e.g. ethyl ether, propylene oxide, tetrahydrofuran or dioxane), an amide (e.g. dimethylacetamide, dimethylpropionamide, dimethylformamide, N-acetylmorpholine, N-acetylpiperidine or N-methylpyrrolidone) or a mixture of these solvents, at a temperature which is slightly lower than for the preparation of the corresponding halogenovinyl derivative, i.e. between −78° and 30° C.

It is also possible to carry out the reaction in the presence of a base such as pyridine, in one of the abovementioned solvents, at a temperature between −78° and 0° C.

The dehydrohalogenation is carried out in the presence of a tertiary base such as defined above, an aromatic amine (e.g. pyridine, picoline or quinoline) or an inorganic base (such as sodium hydroxide, potassium hydroxide, an alkali metal carbonate or bicarbonate or an alkaline earth metal carbonate), in an organic or aqueous-organic medium, in the abovementioned solvents, at a temperature between −20° C. and the reflux temperature of the reaction mixture.

It is not absolutely necessary to have purified the dihalogen intermediate in order to carry out the dehydrohalogenation thereof.

The removal of the various protective radicals can be carried out simultaneously or successively.

By way of example:

1. The removal of the amine-protecting groups is carried out:

in the case of a t-butoxycarbonyl, trityl, p-methoxybenzyloxycarbonyl or formyl radical: by treatment in an acid medium. The acid used in e.g. trifluoroacetic acid, the reaction being carried out at a temperature between 0° and 20° C., or alternatively formic, phosphoric or polyphosphoric acid is used, pure or in the presence of water, at a temperature between 20° C. and 60° C. or p-toluenesulphonic or methanesulphonic acid is used, in acetone or acetonitrile, at a temperature between 20° C. and the reflux temperature of the reaction mixture. Under these conditions, if $R_4$ represents a radical of the general formula (II), the product of the general formula (XIV) can be obtained in the form of the trifluoroacetate, the solvate with formic acid, the phosphate, the methanesulphonate or the p-toluenesulphonate, from which the amine group can be freed by any method which is in itself known for obtaining an amine from one of its salts without affecting the rest of the molecule. The reaction is carried out, in particular, by bringing the compound into contact with an ion exchange resin or by reaction with an organic base;

in the case of a 2,2,2-trichloroethoxycarbonyl or p-nitrobenzyloxycarbonyl radical: by reduction (in particular treatment with zinc in acetic acid);

in the case of a chloroacetyl or trichloroacetyl radical: by applying the method described in the French patent published under No. 2,243,199;

in the case of a benzyl, dibenzyl or benzyloxycarbonyl radical: by catalytic hydrogenation; or in the case of a trifluoroacetyl radical: by treatment in a basic medium.

2. The removal of the protective groups of the carboxyl radical is carried out:

in the case of a t-butyl, p-methoxybenzyl or benzhydryl group: by treatment in an acid medium, under the conditions described above for the removal of the aminoprotecting trityl radical. In the case of the benzhydryl radical, the reaction can be carried out in the presence of anisole;

in the case of a methoxymethyl group: by treatment in a dilute acid medium; or in the case of a nitrobenzyl group: by reduction (in particular treatment with zinc in acetic acid or hydrogenolysis).

3. The removal of the protective groups of the oxime and/or of the hydroxyl radicals is carried out:

in the case of the trityl or tetrahydropyranyl group: by acidolysis, e.g. with trifluoroacetic acid, aqueous or non-aqueous formic acid or p-toluenesulphonic acid;

in the case of the 2-methoxyprop-2-yl group: in accordance with the method described in Belgian Pat. No. 875,379; or in the case of the alkoxycarbonyl or aryloxycarbonyl groups: in accordance with the methods described in Belgian Pat. No. 871,213.

(B) If appropriate, the protective radical $R_4$ is removed (or the protective groups $R_4$ and $R'_1$ are removed simultaneously or successively) from a product of the general formula (XIV) such as defined under (b₁) and of which the radical R" is a hydrogen atom or a methoxy radical in the 7α-position, in order to obtain a product of the general formula:

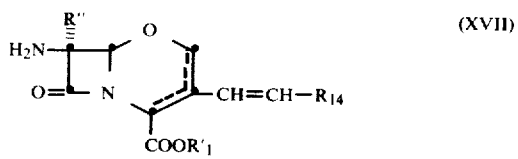

in which $R_{14}$ is defined as for the general formula (XIV), R" is defined as above and $R'_1$ is a hydrogen atom or a protective radical such as defined above for $R_1$.

The removal of the protective radical $R_4$ is carried out by any known method for freeing an amine group without affecting the rest of the molecule.

By way of example, the following methods may be mentioned:

if $R_4$ represents trityl, benzhydryl, trichloroacetyl, chloroacetyl, t-butoxycarbonyl, trichloroethoxycarbonyl, benzyloxycarbonyl, p-methoxybenzyloxycarbonyl and p-nitrobenzyloxycarbonyl: in accordance with the methods mentioned above for the freeing of the amino radical of the product of the general formula (XIV);

if $R_4$ represents formyl, 2-chloro-1,1-dimethylethoxycarbonyl, 2-cyano-1,1-dimethylethoxycarbonyl), 3,5-dimethoxybenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio and p-nitrophenylthio, and if $R_4NH—$ is replaced by dimethylaminomethyleneamino, 3,4-dimethoxybenzylideneamino or 4-nitrobenzylideneamino: by acidolysis;

if $R_4$ represents 3,5-di-t-butyl-4-hydroxybenzylideneamino: by treatment with Girard's T reagent by analogy with the method described in Belgian Pat. No. 863,998;

if $R_4$ represents 2,2,2-trichloroethyl or 2,2,2-trichloro-1,1-dimethylethoxycarbonyl: by treatment with zinc in acetic acid;

if $R_4$ represents acetyl, benzoyl, phenylacetyl or phenoxyacetyl: in accordance with the method described in Belgian Pat. No. 758,800 or in accordance with the method described by YOSHIOKA, Tet. Letters 351 (1980);

if $R_4$ represents trimethylsilylethoxycarbonyl: in accordance with the method described by H. GERLACH, Helv. Chim. Acta 60 (8), 3,039 (1977);

if $R_4$ represents p-nitrobenzyloxycarbonyl and benzyl: by hydrogenolysis in the presence of palladium; or if $R_4$ represents bis-(4-nitrobenzyl)-phosphoryl: by applying the method described in Japanese Patent Application Ser. No. 77/125,185.

If R" is a methoxy group, the following methods can be used in preference to the above methods:

(1) In the case where $R_4$ represents benzhydryl or trityl: hydrogenolysis in the presence of palladium.

(2) In the case where $R_4$ represents radicals of the general formula (IVe) or (IVf): by the method described by E. M. GORDON, J. Amer. Chem. Soc. 102(5), 1,690 (1980); T. KOBAYASHI, Bull. Chem. Soc. Japan 52(11), 3,366 (1979), and T. KOBAYASHI, Chem. Pharm. Bull. 27, 2,718 (1979).

(3) In the case where $R_4$ represents a radical of the general formula (IVg): by acidolysis or by treatment with Girard's T reagent by analogy with the method described in Belgian Pat. No. 863,998.

The oxacephalosporin derivative of the general formula (XVII) is then acylated by reaction with an acid of the general formula (XI) of which the amine group has been protected beforehand if $R_4$ is a radical of the general formula (II), or by reaction with one of its reactive derivatives, and the protective radicals are removed, if appropriate, in order to obtain an oxacephalosporin of the general formula (XIV) in which $R'_1$, $R_{14}$, $R_4$ and $R''$ are defined as above under ($a_1$).

The reaction is carried out under the conditions described below for the reaction of an acid of the general formula (XXIII) or one of its reactive derivatives with a 7-aminooxacephalosporin of the general formula (XXIIa).

If necessary, the removal of the protective radicals is carried out under the conditions described above.

(C) The products of the general formula (XII) are then prepared by reacting a thiol (or one of its alkali metal or alkaline earth metal salts) of the general formula:

R—SH  (XVIII)

[in which R, which is defined as for the products of the general formula (XII), is protected in the form of an acetal (such as defined below) if it is desired to obtain an oxacephalosporin of the general formula (XII) in which R contains a formyl radical] with a product of the general formula (XIV) in which $R'_1$, $R_{14}$, $R_4$ and $R''$ are defined as above under ($a_1$) (or with a mixture of the isomers of this product), and then removing the protective radicals, if necessary.

If it is desired to obtain a product of the general formula (XII) in which R contains a formylalkyl radical, the radical R of the thiol of the general formula (XVIII) is protected as an acetal, in the form of a radical of the general formulae:

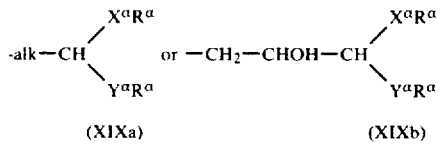

(XIXa)                    (XIXb)

in which alk is an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms.

If the radical R of the product of the general formula (XVIII) is capable of interfering with the reaction, it is preferable to protect this group e.g. by a protective radical defined above (in particular if R contains an amino, alkylamino, hydroxyl or carboxyl radical).

The 2,3-dihydroxypropyl or 1,3-dihydroxyprop-2-yl radicals can be (or are) protected in the form of a 2,2-dimethyldioxolan-4-yl-methyl or 2,2-dimethyldioxan-5-yl radical.

If the radical $R_4$ represents a group of the general formula (II), the amino radical is free or protected, if $R_3$ represents a hydrogen atom, the oxime is preferably protected, and if $R_3$ contains a carboxyl group, the latter is free or protected.

If the radical $R_4$ represents an α-carboxyarylacetyl group, it is preferable to protect the hydroxyl radical if the aryl substituent represents p-hydroxyphenyl; the carboxyl group can be free or protected.

The removal of all these radicals is carried out under the conditions described above.

The removal of the protective radical of R is carried out before, simultaneously with or after the removal of the other protective radicals.

The unblocking of the groups of the general formula (XIXa or b) (if it is desired to obtain a product of the general formula (XII) in which R contains a formylalkyl radical) is carried out:

in the presence of a sulphonic acid (e.g. methanesulphonic acid or p-toluenesulphonic acid), in an organic solvent (e.g. acetonitrile or acetone), if appropriate in the presence of water and if appropriate in the presence of a reagent which can be converted to an acetal, such as acetone, glyoxylic acid, benzaldehyde or pyruvic acid, at a temperature between 20° C. and the reflux temperature of the reaction mixture, or alternatively if the radical R is a 5,6-dioxo-1,4,5,6-tetrahydro-1,2,4-triazin-3-yl radical: by reaction with aqueous formic acid (preferably containing less than 10% of water), either in the presence or absence of silica, or by transacetalisation in the presence of a reagent which can be converted to an acetal, such as defined above.

The freeing of the 2,3-dihydroxypropyl or 1,3-dihydroxyprop-2-yl radicals protected in the form of 2,2-dimethyldioxolan-4-yl-methyl or 2,2-dimethyldioxan-5-yl radicals is carried out by acidolysis, e.g. with trifluoroacetic acid, aqueous or non-aqueous formic acid or p-toluenesulphonic acid.

If aqueous or non-aqueous formic acid is used, the freeing of the hydroxyl radicals protected in the form of a cyclic acetal can lead at least partially to the corresponding monoesters or diesters, which can be separated off by chromatography, if necessary.

The reaction of the thiol of the general formula (XVIII) with the oxacephalosporin derivative of the general formula (XIV) is generally carried out in the presence of an organic base such as a pyridine or a tertiary organic base of the general formula (XVI).

The base used is e.g. diisopropylethylamine or diethylphenylamine.

If an alkali metal salt or alkaline earth metal salt of the thiol of the general formula (XVIII) is reacted, it is not necessary to carry out the reaction in the presence of an organic base such as defined above.

The reaction is advantageously carried out in an organic solvent such as dimethylformamide, tetrahydrofuran or acetonitrile, or a mixture of these solvents.

It is also possible to carry out the reaction in the presence of an alkali metal bicarbonate, in a solvent such as mentioned above, if appropriate in the presence of water.

The reaction is carried out at a temperature between −20° C. and the reflux temperature of the reaction mixture, the chosen temperature varying according to the thiol employed. Likewise, the reaction time can vary from 5 minutes to 48 hours, according to the thiol employed.

If appropriate, the reaction is carried out under nitrogen.

Preferably, if it is desired to use a bicyclooct-3-ene of the general formula (XIV), a product of this type in which $R'_1$ is other than hydrogen is used.

The thiols of the general formula (XVIII), which can be used in their tautomeric form, can be prepared by applying one of the following methods, depending on the meaning of the radical R:

if R is a pyrid-3-yl radical: in accordance with the method described by H. M. WUEST and E. H. SAKAL, J. Amer. Chem. Soc., 73, 1,210 (1951), if R is a pyrid-3-yl-1-oxide radical: in accordance with the method described by B. BLANK et al., J. Med. Chem. 17, 1,065 (1974), if R is a pyrid-4-yl-1-oxide radical: in accordance with the method described by R. A. Y. JONES et al., J. Chem. Soc. 2,937 (1960), if R is a 6-methylpyridazin-3-yl-1-oxide radical: in accordance with the method described in Belgian Pat. No. 787,635, or if R is (1°) a 5,6-dioxo-1,4,5,6-tetrahydro-1,2,4-triazin-3-yl radical substituted in the 4-position by a radical $R^\gamma$ chosen from amongst:

(a) an allyl radical or an alkyl radical (containing 1 or 2 carbon atoms), which is itself optionally substituted by an alkoxy or alkylthio radical, (b) a 2,3-dihydroxypropyl or 1,3-dihydroxyprop-2-yl radical (optionally protected in the form of a cyclic acetal), (c) an alkyl radical (containing 2 or 3 carbon atoms), which is itself substituted [by hydroxyl, carbamoyloxy, dialkylamino, alkylsulphonylamino, acylamino (optionally substituted), ureido, alkylureido or dialkylureido], and (d) a radical of the general formula (XIXa) or (XIXb), or (2°) a 5,6-dioxo-1,4,5,6-tetrahydro-1,2,4-triazin-3-yl radical substituted in the 1-position, or a 5,6-dioxo-1,2,5,6-tetrahydro-1,2,4-triazin-3-yl radical substituted in the 2-position, by an alkyl radical containing 1 or 2 carbon atoms or by a radical of the general formula (XIXa): by reacting an alkyl oxalate with a thiosemicarbazide of the general formulae:

  (XXa)

  (XXb)

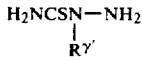  (XXc)

in which $R^\gamma$ has the definition given above under 1°) and $R^{\gamma'}$ is a substituent defined above under 2°), in the presence of an alkali metal alcoholate, e.g. sodium ethylate or methylate or potassium t-butylate, by applying the method described by M. PESSON and M. ANTOINE, Bull. Soc. Chim. France 1,590 (1970).

It is not absolutely necessary to purify the product obtained (or to free the protected radicals) in order to use it for the preparation of the products of the general formula (XII).

The thiosemicarbazide of the general formula (XXa), (XXb) or (XXc) can be prepared in accordance with one of the methods described by K. A. JENSEN et al., Acta Chem. Scand., 22, 1 (1968), or by applying the method described by Y. KAZAKOV and J. Y. POTOVSKII, Doklady Acad. Nauk. SSSR 134, 824 (1960), it being understood that if $R^\gamma$ contains an amino radical, the latter is protected.

The protection of the amino radical and the removal of the protective radical are carried out in accordance with the usual methods which do not affect the rest of the molecule. The t-butoxycarbonyl group, which can be removed by acid hydrolysis, is used in particular.

If R is a 1-alkyl-1,3,4-triazol-5-yl radical: by applying one of the methods described by M. PESSON and M. ANTOINE, Bull. Soc. Chim. France 1,590 (1970).

If R is a 5,6-dioxo-1,4,5,6-tetrahydro-1,2,4-triazin-3-yl radical substituted in the 4-position by acyloxyalkyl (optionally substituted): by acylating 5,6-dioxo-4-hydroxyalkyl-3-mercapto-1,4,5,6-tetrahydro-1,2,4-triazine, the mercapto radical of which has been protected beforehand [e.g. according to C. G. KRUSE et al., Tet. Lett. 1,725 (1976)], by any known method for acylating an alcohol without affecting the rest of the molecule, and then freeing the mercapto group in an acid medium.

If R is a 2-alkyl-5,6-dioxo-1,2,5,6-tetrahydro-1,2,4-triazin-3-yl, 1-alkyl-1,2,4-triazol-5-yl or 1-alkyl-3-alkoxycarbonyl-1,2,4-triazol-5-yl radical: in accordance with the method described by M. PESSON and M. ANTOINE, C. R. Acad. Sci., Series C, 267 (25), 1,726 (1968).

If R is a 2-alkyl-2,5-dihydro-5-oxo-1,2,4-triazin-3-yl radical substituted in the 6-position by an alkyl or alkoxy radical: in accordance with the method described in J. Antibiotics, 33, 783 (1980).

If R is a 1-amino-1,2-dihydro-2-oxopyrimidin-4-yl radical: in accordance with the method described in European Patent Application No. 00,005.

If R is a 1,3,4-thiadiazol-5-yl radical optionally substituted by alkyl: in accordance with the methods described in Belgian Pat. No. 830,821.

If R is a 1,3,4-thiadiazol-5-yl radical substituted by dialkylaminoalkyl: in accordance with the method described in German Patent Application No. 2,446,254.

If R is a 1,3,4-thiadiazol-5-yl radical substituted by an acylaminoalkyl radical: in accordance with the method described in Japanese Patent Application No. 76/80,857.

If R is a tetrazol-5-yl radical optionally substituted in the 1-position by alkyl or hydroxyalkyl: in accordance with the methods described in Belgian Pat. No. 830,821.

If R is a tetrazol-5-yl radical substituted in the 1-position by a dialkylaminoalkyl radical: by applying the method described in German Patent Application No. 2,738,711.

If R is a tetrazol-5-yl radical substituted by an acylaminoalkyl radical: in accordance with the method described in U.S. Pat. No. 4,117,123.

If R is a tetrazol-5-yl radical substituted in the 1-position by a 2,3-dihydroxypropyl radical: in accordance with the method described in U.S. Pat. No. 4,064,242.

If R is a tetrazol-5-yl radical substituted in the 1-position by a 1,3-dihydroxyprop-2-yl radical: by adding sodium azide to a 2,2-dimethyl-1,3-dioxolan-5-yl isothiocyanate (and then, if appropriate, freeing the hydroxyl groups).

If R is a tetrazol-5-yl radical substituted in the 1-position by a radical of the general formula (XIXa): by reacting sodium azide with the corresponding isothiocyanate, by analogy with the method described by R. E. ORTH, J. Pharm. Sci. 52 (9), 909 (1963). II. The 3-thiovinyloxacephalosporins of the general formula (XII) can also be prepared by the following procedure:

(A) A thiol of the general formula (XVIII) of which the radical R is optionally protected, or one of its alkali metal or alkaline earth metal salts, is reacted with an oxacephalosporin derivative, or, if necessary, with a mixture of bicyclooct-2-ene or bicyclooct-3-ene isomers of a derivative of the general formula (XIV) in which R'₁, R₁₄, R₄ and R" are defined as under b₁), in order to obtain an oxacephalosporin derivative of the general formula:

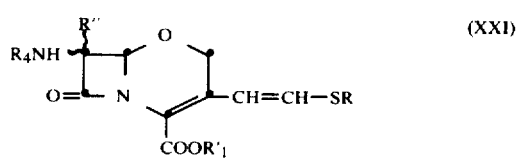
(XXI)

in which R, R'₁, R₄ and R" are defined as above.

The reaction is generally carried out under the conditions described above for the preparation of a 3-thiovinyloxacephalosporin of the general formula (XII) from a thiol of the general formula (XVIII) and a product of the general formula (XIV).

(B) One or other of the following schemes is then followed:

B₁ The radical R₄ is removed (or, if appropriate, the radical R₄ and the other protective radicals are removed successively or simultaneously) from a product of the general formula (XXI), in order to prepare a 7-aminooxacephalosporin of the general formula:

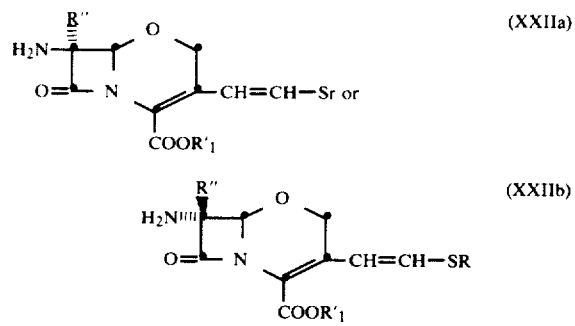
(XXIa)

(XXIb)

in which R'₁ represents a hydrogen atom or a protective radical such as defined above, R is defined as above and R" represents a hydrogen atom or a methoxy radical in the 7α-position in the case of the general formula (XXIIa), or R" represents a hydrogen atom in the 7β-position in the case of the general formula (XXIIb), and then, if R" represents a hydrogen atom in the 7β-position or if it is desired to obtain a product of the general formula (XXIIa) in which R" is methoxy, the oxacephalosporin of the general formula (XXIIa) [in which R" is hydrogen] or (XXIIb) is converted to the corresponding methoxylated derivative.

The removal of the radical R₄ is carried out e.g. under the conditions described above for the preparation of a product of the general formula (XVII) from a product of the general formula (XIV).

The methoxylation is carried out under the conditions described in Japanese Pat. No. 77/125,185 or in Belgian Pat. Nos. 871,213 and 863,998, or in accordance with the methods described by T. KOBAYASHI et al., Chem. Pharm. Bull. 27(11) 2,718 (1979), or by H. YANAGISAWA et al., Tet. Lett., 31, 2,705 (1975).

B₂ Alternatively, if it is desired to obtain a product of the general formula (XXIIa) in which R" is methoxy, an oxacephalosporin of the general formula (XXI) in which R" represents a hydrogen atom in the 7β-position and R₄ represents a radical, which can easily be removed, of the general formula (IVa), (IVe), (IVf) or (IVg) or a bis-(4-nitrobenzyl)-phosphoryl radical is methoxylated, the reaction being carried out under the conditions described above under B₁, and then the radical R₄ is removed (or, if appropriate, the radical R₄ and the other protective radicals are removed).

The freeing of the amino radical is carried out as described above for the preparation of the oxacephalosporin of the general formula (XVII).

(C) An acid of the general formula:

R'—OH (XXIII)

in which R' is defined as above (it being understood that if R' is a radical of the general formula (II), the amine group of this radical is protected), or a reactive derivative of this acid, is then reacted with a 7-aminooxacephalosporin of the general formula (XXIIa) and the protective groups are then removed.

If R' represents a radical of the general formula (II), the acid of the general formula (XXIII) in the syn or anti form, or mixtures thereof, leads respectively to the products of the general formula (I) in the syn or anti form, or to mixtures thereof.

It is understood that the oxime is protected if R₃ represents a hydrogen atom.

If R₃ contains a carboxyl radical, the latter is also protected.

If R' represents an α-carboxyarylacetyl radical, the protection of the carboxyl group is not obligatory; the latter can therefore be free or protected.

The same applies to the hydroxyl radical if the aryl group represents p-hydroxyphenyl.

If R contains an amino or alkylamino substituent, this group is protected, and if it contains one or more hydroxyl substituents, the latter are free or preferably protected.

It is understood that the amino, alkylamino, carboxyl and hydroxyl groups which exist in certain radicals are (or can be) protected by any groups which are normally used for protecting amines, carboxylic acids, alcohols or oximes, and the use of which does not affect the rest of the molecule.

By way of example, protective groups such as mentioned above are used.

If it is desired to obtain a product of the general formula (XII) in which R contains a formylalkyl radical, this radical can be optionally protected as an acetal, in the form of a radical of the general formula (XIXa) or (XIXb). This radical can be removed under the conditions described above.

(a) If the product of the general formula (XXIII) is used in the form of the acid, this product (of which the amine and/or oxime groups have been protected beforehand, if necessary) is generally condensed with the 7-aminooxacephalosporin of the general formula (XXIIa) in which, R being defined as above, R'₁ represents a protective radical which can easily be removed, the reaction being carried out in an organic solvent such as dimethylformamide, acetonitrile, tetrahydrofuran, methylene chloride or chloroform, in the presence of a condensation agent such as a carbodiimide (e.g. dicyclohexylcarbodiimide), N,N'-carbonyldiimidazole or 2-ethoxy-1-ethoxycarbonyl-1,2-dihydroquinoline, at a temperature between −20° and 40° C., and the protective groups present in the molecule are then removed. If appropriate, the reaction is carried out in the presence of a catalytic amount of 4-N,N-dimethylaminopyridine.

(b) If a reactive derivative of the acid of the general formula (XXIII) is used, it is possible to use the anhydride, a mixed anhydride or a reactive ester of the general formula:

R'—OZ (XXIV)

in which R' is defined as above and Z represents a succinimido, benzotriazol-1-yl, 4-nitrophenyl, 2,4-dinitrophenyl, pentachlorophenyl or phthalimido radical. If R' is a radical of the general formula (II), the amine group of such derivatives is protected beforehand (e.g. as described above). The conditions for protecting the various substituents are such as described above.

It is also possible to use a reactive derivative such as an acid halide. In the latter case, if R' is a radical of the general formula (II), it is possible e.g. to react the hydrochloride of the acid chloride with the 7-aminooxacephalosporin of the general formula (XXIIa). If R' is an α-carboxy-(p-hydroxyphenyl)-acetyl radical, the hydroxyl group can be free or protected.

If the anhydride, a mixed anhydride or an acid halide (which can all be prepared in situ) is used, the condensation is carried out in an inert organic solvent such as an ether (e.g. tetrahydrofuran or dioxane), a chlorinated solvent (e.g. chloroform or methylene chloride), an amide (e.g. dimethylformamide or dimethylacetamide) or a ketone (e.g. acetone), or in mixtures of these solvents, in the presence of an acid acceptor such as an epoxide (e.g. propylene oxide) or such as a nitrogen-containing organic base like pyridine, dimethylaminopyridine, N-methylmorpholine or a trialkylamine (e.g. triethylamine), or in an aqueous-organic medium, in the presence of an alkaline condensation agent such as sodium bicarbonate, and the reaction is carried out at a temperature between −40° and +40° C., and the protective groups are then replaced, if appropriate, by hydrogen atoms.

If a reactive ester of the general formula (XXIV) is used, the reaction is generally carried out in the presence of a trialkylamine (e.g. triethylamine), in an organic solvent such as dimethylformamide, at a temperature between 0° and 40° C., and the protective groups are then replaced by hydrogen atoms.

The isomers of the products of the general formulae (I), (V), (VIII), (IXa), (XII), (XIV), (XIVa), (XVII), (XXI), (XXIIa) and (XXIIb) can be separated by chromatography or crystallisation.

The new oxacephalosporin derivatives of the general formula (XII) and their pharmaceutically acceptable salts possess particularly valuable antibacterial properties. They show a remarkable in vitro and in vivo activity against Gram-positive and Gram-negative germs.

In vitro, the products of the general formula (XII) have been shown to be active at a concentration of between 1 and 15 μg/cc against staphylococcus strains sensitive to penicillin G (Staphylococcus aureus Smith) and at a concentration of between 0.01 and 1 μg/cc against Escherichia coli, NIHJ strain.

In vivo, the products of the general formula (XII) have been shown to be active at a daily dose of between 0.5 and 15 mg/kg, administered subcutaneously, against experimental infections caused in mice by Staphylococcus aureus Smith (sensitive to penicillin G), and at daily doses of between 0.01 and 10 mg/kg, administered subcutaneously, against experimental infections caused in mice by Escherichia coli NIHJ strain.

Furthermore, the $LD_{50}$ of the products of the general formula (XII) is between 1.5 g/kg and doses of more than 2.5 g/kg, administered subcutaneously to mice.

Of particular value are the oxacephalosporins of the general formula (I), in the form of a bicyclooct-2-ene, in which $R_1$ represents a benzhydryl or nitrobenzyl radical, $R_4$ represents a radical of the general formula (II) or a radical which can easily be removed [chosen from amongst trityl or the radicals of the general formulae (IVa) and (IVd)] and R" represents a hydrogen atom or a methoxy radical in the 7α-position, and, amongst these products, more especially the products of the general formula (I), in the form of a bicyclooct-2-ene, in which $R_1$ represents a benzhydryl or p-nitrobenzyl radical, $R_4$ represents a radical of the general formula (II) [in which $R_2$ represents an amino-protecting radical and $R_3$ represents an alkyl radical] or a radical which can easily be removed, chosen from amongst trityl or the radicals of the general formula (IVa) [in which $R_5$ represents a radical of the general formula (IVb) in which Y represents an oxygen atom, or a radical of the general formula (IVc)], or the radicals of the general formula (IVd) in which $R_6$ represents an alkyl radical, and R" represents a hydrogen atom or a methoxy radical in the 7α-position, and, in particular: 2-benzhydryloxycarbonyl-3-(2-oxoethyl)-8-oxo-7-tritylamino-5-oxa-1-azabicyclo[4.2.0]oct-2-ene, 2-benzhydryloxycarbonyl-3-(2-oxoethyl)-8-oxo-7-phenylacetamido-5-oxa-1-azabicyclo[4.2.0]oct-2-ene, 2-benzhydryloxycarbonyl-7α-methoxy-3-(2-oxoethyl)-8-oxo-7β-phenoxyacetamido-5-oxa-1-azabicyclo[4.2.0]oct-2-ene and 2-benzhydryloxycarbonyl-7-[2-methoxyimino-2-(2-tritylaminothiazol-4-yl)acetamido]-3-(2-oxoethyl)-8-oxo-5-oxa-1-azabicyclo[4.2.0]oct-2-ene.

The following examples, which are given without implying a limitation, show how the invention can be put into practice.

In these examples, the products are named according to the nomenclature of Chemical Abstracts. It is understood that, unless otherwise mentioned, the oxacephalosporin derivatives mentioned exhibit the stereochemistry given by the partial general formula:

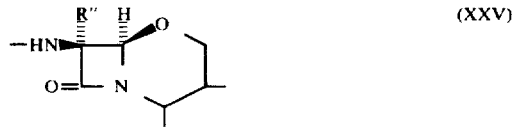

(XXV)

in which R" is in the 7α-position.

EXAMPLE 1

A solution of the E form of 2-benzhydryloxycarbonyl-3-(2-dimethylaminovinyl)-8-oxo-7-tritylamino-5-oxa-1-azabicyclo[4.2.0]oct-2-ene (3.0 g) in ethyl acetate (100 cc) is stirred vigorously for 1 hour 30 minutes at 20° C., in the presence of a 1 N solution of hydrochloric acid (45 cc). The mixture is separated by decantation and the organic phase is washed with a 5% strength solution of sodium bicarbonate (50 cc) and then with a semi-saturated solution of sodium chloride (50 cc). The ethyl acetate phase is dried over sodium sulphate and filtered and the filtrate is concentrated to dryness at 30° C. under reduced pressure (20 mm Hg; 2.7 kPa). This yields a crude product (2.52 g) consisting mainly of 2-benzhydryloxycarbonyl-8-oxo-3-(2-oxoethyl)-7- tritylamino-5-oxa-1-aza-bicyclo[4.2.0]oct-2-ene in the form of a hard, light chestnut-coloured foam.

Infra-red spectrum (KBr), characteristic bands (cm$^{-1}$): 1,790, 1,720, 1,600, 1,495, 1,450, 1,220, 750, 700.

Proton NMR spectrum (350 MHz, CDCl$_3$, δ in ppm, J in Hz): 3.37 and 3.50 (2d, J=16, 2H,

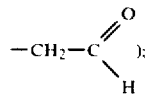

3.81 (d, J=3.5, 1H, H in the 6-position); 3.92 and 4.12 (2d, J=18, 2H, —CH$_2$—O—); 4.35 (dd, J=3.5 and 9, 1H, H in the 7-position); 6.80 (s, 1H, —COO—CH(C$_6$H$_5$)$_2$); 9.49 (s, 1H,

The E form of 2-benzhydryloxycarbonyl-3-(2-dimethylaminovinyl)-8-oxo-7-tritylamino-5-oxa-1-azabicyclo-[4.2.0]oct-2-ene can be obtained in the following manner:

A solution of 2-benzhydryloxycarbonyl-3-methyl-8-oxo-7-tritylamino-5-oxa-1-azabicyclo[4.2.0]oct-2-ene (4.25 g) in dimethylformamide (20 cc) is heated to 80° C. under nitrogen. t-Butoxy-bis-dimethylaminomethane (1.55 cc) is added dropwise, in the course of 7 minutes, to the solution stirred at 80° C. When the addition has ended, the mixture is stirred at 80° C. for 17 minutes. The solution is diluted with ethyl acetate (150 cc), the organic phase is washed with distilled water (3×60 cc) and a semi-saturated solution of sodium chloride (60 cc), dried over sodium sulphate and filtered and the filtrate is concentrated to dryness at 30° C. under reduced pressure (20 mm Hg; 2.7 kPa). The residue is triturated in ethyl ether (150 cc), the suspension obtained is filtered and the filtrate is concentrated to dryness at 30° C. under reduced pressure (20 mm Hg; 2.7 kPa). This yields a crude product (3.14 g) consisting mainly of the E form of 2-benzhydryloxycarbonyl-3-(2-dimethylaminovinyl)-8-oxo-7-tritylamino-5-oxa-1-azabicyclo[4.2.0]oct-2-ene, which can be used without further purification.

Infra-red spectrum (KBr), characteristic bands (cm$^{-1}$): 1,780, 1,660, 1,615, 1,490, 1,450, 745, 700.

Proton NMR spectrum (350 MHz, CDCl$_3$, δ in ppm, J in Hz): 2.77 (s, 6H, —N(CH$_3$)$_2$); 3.71 (d, J=3.5, 1H, H in the 6-position); 4.12 and 4.53 (2d, J=17, 2H, —CH$_2$—O—); 4.26 (m, 1H, H in the 7-position); 6.24 and 6.40 (2d, J=13, 2H, —CH=CH—); 6.81 (s, 1H, —COO—CH(C$_6$H$_5$)$_2$).

2-Benzhydryloxycarbonyl-3-methyl-8-oxo-7-tritylamino-5-oxa-1-azabicyclo[4.2.0]oct-2-ene (7.74 g) is prepared according to a synthesis scheme described in U.S. Pat. No. 4,108,992, in which the t-butyl glyoxylate is replaced by the benzhydryl glyoxylate prepared according to French Pat. No. 1,495,047.

The expected oxacephalosporin is obtained in the form of a white solid from 2-oxo-4-(prop-2-ynyloxy)-3-tritylaminoazetidine (13.2 g).

Infra-red spectrum (KBr), characteristic bands (cm$^{-1}$): 3,340, 1,780, 1,715, 1,620, 1,595, 1,585, 1,490, 1,450, 1,220, 745, 700.

Proton NMR spectrum (350 MHz, CDCl$_3$, δ in ppm, J in Hz): 1.90 (s, 3H, —CH$_3$); 3.75 (d, J=3.5, 1H, H in the 6-position); 3.87 and 4.08 (2d, J=18, 2H, —CH$_2$—O—); 4.30 (d, J=3.5, 1H, H in the 7-position); 6.85 (s, 1H, —COO—CH(C$_6$H$_5$)$_2$); 7.15 to 7.4 (m, 26H, aromatic protons and —HN—C(C$_6$H$_5$)$_3$).

EXAMPLE 2

A solution of the E form of the syn isomer of 2-benzhydryloxycarbonyl-3-(2-dimethylaminovinyl)-7-[2-methoxyimino-2-(2-tritylaminothiazol-4-yl)-acetamido]-8-oxo-5-oxa-1-azabicyclo[4.2.0]oct-2-ene (1.05 g) in ethyl acetate (10 cc) is stirred vigorously for 1 hour at 20° C., in the presence of a 1 N solution of hydrochloric acid (5 cc). The mixture is separated by decantation and the organic phase is washed with a saturated solution of sodium bicarbonate (10 cc), distilled water (10 cc) and a saturated solution of sodium chloride (10 cc). The ethyl acetate phase is dried over anhydrous magnesium sulphate and filtered and the filtrate is concentrated to dryness at 30° C. under reduced pressure (20 mm Hg; 2.7 kPa). This yields the syn isomer of 2-benzhydryloxycarbonyl-7-[2-methoxyimino-2-(2-tritylaminothiazol-4-yl)-acetamido[-8-oxo-3-(2-oxoethyl)-5-oxa-1-azabicyclo[4.2.0]-oct-2-ene (1.00 g) in the form of a hard yellow foam.

Infra-red spectrum (KBr), characteristic bands (cm$^{-1}$): 3,400, 1,795, 1,725, 1,685, 1,525, 1,495, 1,450, 1,035, 755, 700.

Mass spectrum: molecular peak=817.

Proton NMR spectrum (250 MHz, CDCl$_3$, δ in ppm, J in Hz): 3.52 (d, J=16.25, 1H, —CH$_2$CHO); 3.62 (d, J=16.25, 1H, —CH$_2$—CHO); 4.07 (s, 3H, =NOCH$_3$); 4.35 (s, 2H, —CH$_2$O—); 5.17 (d, J=3.75, 1H, —H in the 6-position); 5.82 (dd, J=10 and 3.75, 1H, —H in the 7-position); 6.76 (d, J=10, 1H, —CONH—); 6.80 (s, 1H, —H of the thiazole); 6.85 (s, 1H, —COOCH(C$_6$H$_5$)$_2$); 7.13 (m, 1H, (C$_6$H$_5$)$_3$CNH—); 7.20 to 7.55 (m, 25H, aromatic protons); 9.60 (s, 1H, —CHO).

The E form of the syn isomer of 2-benzhydryloxycarbonyl-3-(2-dimethylaminovinyl)-7-[2-methoxyimino-2-(2-tritylaminothiazol-4-yl)-acetamido]-8-oxo-5-oxa-1-azabicyclo[4.2.0]oct-2-ene can be obtained in the following manner:

A solution of the syn isomer of 2-benzhydryloxycarbonyl-7-[2-methoxyimino-2-(2-tritylaminothiazol-4-yl)acetamido]-3-methyl-8-oxo-5-oxa-1-azabicyclo[4.2.0]oct-2-ene (0.79 g) in dimethylformamide (5 cc) is heated to 80° C. under nitrogen. t-Butoxy-bis-dimethylaminomethane (0.2 cc) is added dropwise, in the course of 6 minutes, to the solution stirred at 80° C. When the addition has ended, the mixture is stirred at 80° C. for 20 minutes. The solution is diluted with ethyl acetate (25 cc), the organic phase is washed with distilled water (3×25 cc) and a saturated solution of sodium chloride (25 cc), dried over magnesium sulphate and filtered and the filtrate is concentrated to dryness at 40° C. under reduced pressure (20 mm Hg; 2.7 kPa). This yields a crude product (0.71 g) consisting mainly of the E form of the syn isomer of 2-benzhydryloxycarbonyl-3-(2-dimethylaminovinyl)-7-[2-methoxyimino-2-(2-tritylaminothiazol-4-yl)-acetamido]-8-oxo-5-oxa-1-azabicyclo[4.2.0]oct-2-ene.

A sample (0.4 g) is purified by chromatography on a column of silica (0.04–0.06) (diameter of the column: 2.2 cm; height: 20 cm), elution being carried out under 50 kPa with a mixture of cyclohexane and ethyl acetate (40/60 by volume) and 40 cc fractions being collected.

Fractions 9 to 15 are combined and concentrated to dryness under reduced pressure (30 mm Hg; 4 kPa) at 40° C. This yields a yellow powder (0.020 g) of the pure product.

Mass spectrum: molecular peak=844.

Proton NMR spectrum (350 MHz, CDCl$_3$, δ in ppm, J in Hz): 2.86 (s, 6H, —N(CH$_3$)$_2$); 4.07 (s, 3H, =NOCH$_3$); 4.61 and 4.76 (2d, J=18, 2H, —CH$_2$O—); 5.10 (d, J=3.5, 1H, H in the 6-position); 5.69 (dd, J=3.5 and 9, 1H, H in the 7-position); 6.36 and 6.54 (2d, J=14, 2H, —CH=CH—); 6.67 (d, J=9, 1H, —CONH—); 6.82 (d, 1H, H of the thiazole); 6.86 (s, 1H, —CO$_2$CH(C$_6$H$_5$)$_2$); 7.01 (s, 1H, —NHC(C$_6$H$_5$)$_3$); 7.15 to 7.65 (m, 25H).

Infra-red spectrum (KBr), characteristic bands (cm$^{-1}$): 1,780, 1,685, 1,615, 1,525, 1,490, 1,445, 1,120, 1,030, 740, 695.

The syn isomer of 2-benzhydryloxycarbonyl-7-[2-methoxyimino-2-(2-tritylaminothiazol-4-yl)-acetamido]-3-methyl-8-oxo-5-oxa-1-azabicyclo[4.2.0]oct-2-ene can be prepared in the following manner:

A solution of 7-amino-2-benzhydryloxycarbonyl-3-methyl-8-oxo-5-oxa-1-azabicyclo[4.2.0]oct-2-ene tosylate (35 g) in ethyl acetate (50 cc) is washed with a 1 N solution of sodium bicarbonate (15 cc) and distilled water (50 cc) and then dried over magnesium sulphate. After filtration, the solvent is evaporated off under reduced pressure (20 mm Hg; 2.7 kPa) at 40° C. This yields 7-amino-2-benzhydryloxycarbonyl-3-methyl-8-oxo-5-oxa-1-azabicyclo[4.2.0]oct-2-ene (2.33 g) in the form of a hard, pale yellow foam.

Mass spectrum: molecular peak=364.

Infra-red spectrum (KBr), characteristic bands (cm$^{-1}$): 3,400, 3,340, 1,780, 1,720, 1,640, 1,495, 1,445, 1,230, 1,110, 1,060, 745, 700.

Proton NMR spectrum (350 MHz, CDCl$_3$, δ in ppm, J in Hz): 2.03 (s, 3H, —CH$_3$); 4.32 (s, 2H, —CH$_2$O—); 4.47 (d, J=3.5, 1H, —H in the 7-position); 4.92 (d, J=3.5, 1H, —H in the 6-position); 6.90 (s, 1H, —CO$_2$CH(C$_6$H$_5$)$_2$); 7.15 to 7.45 (m, 10H, aromatic protons).

A solution of N,N'-dicyclohexylcarbodiimide (1.56 g) and 4-N,N-dimethylaminopyridine (0.001 g) in methylene chloride (40 cc) is added, in the course of 15 minutes, to a solution of 7-amino-2-benzhydryloxycarbonyl-3-methyl-8-oxo-5-oxa-1-azabicyclo[4.2.0]oct-2-ene (2.3 g) and the syn isomer of 2-methoxyimino-2-(2-tritylaminothiazol-4-yl)-acetic acid (2.79 g) in methylene chloride (50 cc). The mixture is stirred at 0° C. for 2 hours. It is subsequently transferred into a separating funnel and then washed successively with a 0.1 N solution of hydrochloric acid (50 cc), distilled water (50 cc), a semi-saturated solution of sodium bicarbonate (50 cc) and then distilled water (50 cc). The methylene chloride phase is dried over anhydrous magnesium sulphate. When the drying agent has been filtered off, the solution is concentrated to dryness under reduced pressure (100 mm Hg; 13.5 kPa). The residue (5.6 g) is purified by chromatography on a column of silica (0.04–0.06) (diameter of the column: 5.6 cm; height: 26 cm), elution being carried out under 50 kPa with a mixture of cyclohexane and ethyl acetate (50/50 by volume) and 120 cc fractions being collected. Fractions 8 to 20 are combined and concentrated to dryness under reduced pressure (30 mm Hg; 4 kPa) at 40° C. This yields a hard beige foam (4.02 g) of the pure syn isomer of 2-benzhydryloxycarbonyl-7-[2-methoxyimino-2-(2-tritylamino-thiazol-4-yl)-acetamido]-3-methyl-8-oxo-5-oxa-1-azabicyclo[4.2.0]oct-2-ene.

Mass spectrum: molecular peak=789.

Infra-red spectrum (KBr), characteristic bands (cm$^{-1}$): 2,820, 1,790, 1,745, 1,580, 1,530, 1,495, 1,450, 1,165, 1,040, 750, 700.

Proton NMR spectrum (350 MHz, CDCl$_3$, δ in ppm, J in Hz): 2.04 (s, 3H, —CH$_3$); 4.07 (s, 3H, =N—OCH$_3$); 4.32 (s, 2H, —CH$_2$O—); 5.12 (d, J=3.5, 1H, —H in the 6-position); 5.75 (dd, J=3.5 and 9, 1H, —H in the 7-position); 6.68 (d, J=9, 1H, —CONH—); 6.79 (s, 1H, H of the thiazole); 6.89 (s, 1H, —CO$_2$CH(C$_6$H$_5$)$_2$); 7.00 (s broad, 1H, —NHC(C$_6$H$_5$)$_3$); 7.15 to 7.55 (m, 25H, aromatic protons).

7-Amino-2-benzhydryloxycarbonyl-3-methyl-8-oxo-5-oxa-1-azabicyclo[4.2.0]oct-2-ene tosylate can be obtained in the following manner:

A solution of 2-benzhydryloxycarbonyl-3-methyl-8-oxo-7-tritylamino-5-oxa-1-azabicyclo[4.2.0]oct-2-ene (6.07 g) and p-toluenesulphonic acid hydrate (1.9 g) in acetone (100 cc) is stirred at 40° C. for 30 minutes. The mixture is cooled to 0° C. and a white solid precipitates. It is filtered off and the cake is washed with acetone (2×5 cc). This yields 7-amino-2-benzhydryloxycarbonyl-3-methyl-8-oxo-5-oxa-1-azabicyclo[4.2.0]oct-2-ene tosylate (3.17 g).

The acetone filtrate is concentrated to dryness under reduced pressure (20 mm Hg; 2.7 kPa). The residue is triturated in ethyl ether (2×100 cc). The ether is decanted and the solid obtained is taken up in ethyl acetate (20 cc). The mixture is filtered and a second fraction of 7-amino-2-benzhydryloxycarbonyl-3-methyl-8-oxo-5-oxa-1-azabicyclo[4.2.0]oct-2-ene tosylate (0.72 g) is obtained.

Infra-red spectrum (CHBr$_3$), characteristic bands (cm$^{-1}$): 3,300, 2,400, 1,800, 1,720, 1,500, 1,455, 1,225, 820, 760, 745, 570.

Proton NMR spectrum (350 MHz, CDCl$_3$, δ in ppm, J in Hz): 1.73 (s, 3H, —CH$_3$); 2.15 (s, 3H, —CH$_3$ (PTSA)); 3.98 (d, J=19, 1H, —CH$_2$O—); 4.11 (d, J=19, 1H, —CH$_2$O—); 4.78 (d, J=2.5, 1H, —H in the 7-position); 4.86 (d, J=2.5, 1H, —H in the 6-position); 6.87 (s, 1H, —COOCH(C$_6$H$_5$)$_2$); 6.96 (d, J=7.5, 1H, —H in the ortho-position to the methyl, PTSA); 7.10 to 7.60 (m, 10H, aromatic protons); 7.74 (d, J=7.5, 1H, —H in the ortho-position to the SO$_3$H, PTSA), 8.60 (m, 3H, —NH$_3$$^+$).

EXAMPLE 3

A solution of the E form of 2-benzhydryloxycarbonyl-7-t-butoxycarbonylamino-3-(2-dimethylaminovinyl)-8-oxo-5-oxa-1-azabicyclo[4.2.0]oct-2-ene (obtained as described below) (0.16 g) in ethyl acetate (5 cc) is stirred vigorously for 30 minutes at 20° C., in the presence of a 1 N solution of hydrochloric acid (3 cc). The mixture is separated by decantation and the organic phase is washed with a 5% strength solution of sodium bicarbonate (5 cc), distilled water (5 cc) and then a semi-saturated solution of sodium chloride (5 cc). The ethyl acetate phase is dried over anhydrous magnesium sulphate and filtered and the filtrate is concentrated to dryness at 30° C. under reduced pressure (20 mm Hg; 2.7 kPa). This yields 2-benzhydryloxycarbonyl-7-t-butoxycarbonylamino-3-(2-oxoethyl)-8-oxo-5-oxa-1-azabicyclo[4.2.0]oct-2-ene (0.11 g) in the form of a hard, light chestnut-coloured foam.

Mass spectrum: molecular peak=492.

Infra-red spectrum (KBr), characteristic bands (cm$^{-1}$): 1,790, 1,720, 1,515, 1,500+1,455, 1,390, 1,370, 1,165, 750, 700.

Proton NMR spectrum (350 MHz, CDCl$_3$, δ in ppm. J in Hz): 1.47 (s, 9H, —C(CH$_3$)$_3$); 3.52 (d, J=16, 1H, —CH$_2$—CHO); 3.62 (d, J=16, 1H, —CH$_2$—CHO); 4.36 (limiting AB-type, J=17.5, 2H, —CH$_2$—O—); 5.10 (d, J=3.5, 1H, —H in the 6-position); 5.27 (d, J=10.5, 1H, —CONH—); 5.47 (dd, J=10.5 and 3.5, 1H, —H in the 7-position); 6.87 (s, 1H, —COOCH(C$_6$H$_5$)$_2$); 7.20 to 7.60 (m, 10H, aromatic protons); 9.58 (s, 1H, —CHO).

The E form of 2-benzhydryloxycarbonyl-7-t-butoxycarbonylamino-3-(2-dimethylaminovinyl)-8-oxo-5-oxa-1-azabicyclo[4.2.0]oct-2-ene can be obtained in the following manner:

A solution of 2-benzhydryloxycarbonyl-7-t-butoxycarbonylamino-3-methyl-8-oxo-5-oxa-1-azabicyclo[4.2.0]oct-2-ene (1.29 g) in dimethylformamide (15 cc) is heated to 80° C. under nitrogen. t-Butoxy-bis-dimethylaminomethane (0.7 cc) is added dropwise, in the course of 5 minutes, to the solution stirred at 80° C. When the addition has ended, the mixture is stirred for 20 minutes. The solution is diluted with ethyl acetate (100 cc), the organic phase is washed with distilled water (3×50 cc) and a saturated solution of sodium chloride (50 cc), dried over magnesium sulphate and filtered and the filtrate is concentrated to dryness at 30° C. under reduced pressure (20 mm Hg; 2.7 kPa). This yields a crude product (1.10 g) consisting mainly of the E form of 2-benzhydryloxycarbonyl-7-t-butoxycarbonylamino-3-(2-dimethylaminovinyl)-8-oxo-5-oxa-1-azabicyclo[4.2.0]oct-2-ene.

This product (1.04 g) is chromatographed on a column of silica (0.04–0.06) (diameter of the column: 4.5 cm; height: 25 cm), elution being carried out under 50 kPa with a mixture of cyclohexane and ethyl acetate (60/40 by volume) and 50 cc fractions being collected. Fractions 7 to 10 are combined and concentrated to dryness under reduced pressure (30 mm Hg; 4 kPa) at 40° C. This yields a hard yellow foam (0.4 g) consisting of a mixture (44/56 in mols) of the E form of 2-benzhydryloxycarbonyl-7-t-butoxycarbonylamino-3-(2-dimethylaminovinyl)-8-oxo-5-oxa-1-azabicyclo[4.2.0]oct-2-ene and the corresponding 3-(2-oxoethyl) product.

Physical characteristics of the E form of 2-benzhydryloxycarbonyl-7-t-butoxycarbonylamino-3-(2-dimethylaminovinyl)-8-oxo-5-oxa-1-azabicyclo[4.2.0]oct-2-ene:

Mass spectrum: molecular peak=519.

Infra-red spectrum (KBr), characteristic bands (cm$^{-1}$): 3,400, 2,980, 2,925, 2,850, 1,785, 1,715, 1,615, 1,515, 1,500, 1,455, 1,245, 1,175, 1,100, 1,070, 750, 700.

Proton NMR spectrum (350 MHz, CDCl$_3$, δ in ppm, J in Hz): 1.47 (s, 9H, —C(CH$_3$)$_3$); 2.85 (s, 6H, —N(CH$_3$)$_2$); 4.61 (d, J≈16, 1H, —CH$_2$O—); 4.77 (d, J=16, 1H, —CH$_2$O—); 5.10 (d, J=3.5, 1H, —H in the 6-position); 5.30 (d, J=10.5, 1H, —CONH—); 5.38 (dd, J=10.5 and 3.5, 1H, —H in the 7-position); 6.36 (d, J=14, 1H, —CH=CH—); 6.53 (d, J=14, 1H, —CH=CH—); 6.88 (s, 1H, —COOCH(C$_6$H$_5$)$_2$); 7.14 to 7.70 (m, 10H, aromatic protons).

2-Benzhydryloxycarbonyl-7-t-butoxycarbonylamino-3-methyl-8-oxo-5-oxa-1-azabicyclo[4.2.0]oct-2-ene can be obtained in the following manner:

7-Amino-2-benzhydryloxycarbonyl-3-methyl-8-oxo-5-oxa-1-azabicyclo[4.2.0]oct-2-ene (1 g), sodium bicarbonate (0.45 g) and di t-butyl pyrocarbonate (0.65 g) are stirred for 4 hours, at 20° C., in a mixture of distilled water (4 cc) and dioxane (8 cc). The mixture is concentrated under reduced pressure (20 mm Hg; 2.7 kPa) to a residual volume of 5 cc. The residue is diluted in ethyl acetate (10 cc) and the organic phase is washed with distilled water (10 cc) and dried over magnesium sulphate. The mixture is filtered and the filtrate is evaporated under reduced pressure (20 mm Hg; 2.7 kPa). This yields 2-benzhydryloxycarbonyl-7-t-butoxycarbonylamino-3-methyl-8-oxo-5-oxa-1-azabicyclo[4.2.-0]oct-2-ene (1.25 g) in the form of a hard, pale yellow foam.

Mass spectrum: molecular peak=464.

Infra-red spectrum (KBr), characteristic bands (cm$^{-1}$): 3,380, 1,790, 1,720, 1,640, 1,515, 1,500, 1,220, 1,170, 750, 700.

Proton NMR spectrum (350 MHz, CDCl$_3$, δ in ppm, J in Hz): 1.48 (s, 9H, —C(CH$_3$)$_3$); 2.04 (s, 3H, —CH$_3$); 4.32 (s, 2H, —CH$_2$O—); 5.05 (d, J=3.5, 1H, —H in the 6-position); 5.26 (d, J=10.5, 1H, —CONH—); 5.43 (dd, J=3.5 and 10.5, 1H, H in the 7-position); 6.89 (s, 1H, —CO$_2$CH(C$_6$H$_5$)$_2$); 7.23 to 7.60 (m, 10H, aromatic protons).

EXAMPLE 4

A solution of the E form of 2-benzhydryloxycarbonyl-3-(2-dimethylaminovinyl)-8-oxo-7-phenylacetamido-5-oxa-1-azabicyclo[4.2.0]oct-2-ene (obtained under the conditions described below) (0.02 g) in ethyl acetate (5 cc) is stirred vigorously for 30 minutes at 20° C., in the presence of 1 N solution of hydrochloric acid (3 cc). The mixture is separated by decantation and the organic phase is washed with distilled water (10 cc), a 5% strength solution of sodium bicarbonate (10 cc), distilled water (10 cc) and a semi-saturated solution of sodium chloride (10 cc). The ethyl acetate phase is dried over anhydrous magnesium sulphate and filtered and the filtrate is concentrated to dryness at 30° C. under reduced pressure (20 mm Hg; 2.7 kPa). This yields 2-benzhydryloxycarbonyl-3-(2-oxoethyl)-8-oxo-7-phenylacetamido-5-oxa-1-azabicyclo[4.2.0]oct-2-ene (0.02 g) in the form of a light yellow powder.

Mass spectrum: molecular peak=510.

Infra-red spectrum (KBr), characteristic bands (cm$^{-1}$): 3,420, 3,370, 2,930, 2,860, 2,740, 1,792, 1,720, 1,685, 1,670, 1,650, 1,530, 1,500, 1,460, 1,230, 1,110, 1,070, 760, 750, 705.

Proton NMR spectrum (350 MHz, CDCl$_3$, δ in ppm, J in Hz): 3.48 (d, J=17.5, 1H, —CH$_2$CHO); 3.54 (d, J=17.5, 1H, —CH$_2$CHO); 3.65 (s, 2H, C$_6$H$_5$—CH$_2$—); 4.22 (limiting AB-type, J≈16, 2H, —CH$_2$—O—); 5.05 (d, J=3.5, 1H, —H in the 6-position); 5.74 (dd, J=10 and 3.5, 1H, —H in the 7-position); 6.28 (d, J=10, 1H, —CO—NH—); 6.84 (s, 1H, —COOCH(C$_6$H$_5$)$_2$); 7.10 to 7.60 (m, 15H, aromatic protons); 9.53 (s, 1H, —CHO).

The E form of 2-benzhydryloxycarbonyl-3-(2-dimethylaminovinyl)-8-oxo-7-phenylacetamido-5-oxa-1-azabicyclo[4.2.0]oct-2-ene can be obtained in the following manner:

A solution of 2-benzhydryloxycarbonyl-3-methyl-8-oxo-7-phenylacetamido-5-oxa-1-azabicyclo[4.2.0]oct-2-ene (0.527 g) in dimethylformamide (5 cc) is heated to 80° C. under nitrogen. t-Butoxy-bis-dimethylaminomethane (0.25 cc) is added dropwise, in the course of 4 minutes, to the solution stirred at 80° C. When the addition has ended, the mixture is stirred at 80° C. for 20 minutes. The solution is diluted with ethyl acetate (25 cc), the organic phase is washed with distilled water (5×25 cc) and a saturated solution of sodium chloride (25 cc), dried over magnesium sulphate and filtered and the filtrate is concentrated to dryness at 40° C. under reduced pressure (20 mm Hg; 2.7 kPa). This yields a crude product (0.44 g) consisting mainly of the E form of 2-benzhydryloxycarbonyl-3-(2-dimethylaminovinyl)-8-oxo-7-phenylacetamido-5-oxa-1-azabicyclo[4.2.0]oct-2-ene.

This product (0.4 g) is chromatographed on a column of silica (0.04–0.06) (diameter of the column: 3.9 cm; height: 24 cm), elution being carried out under 50 kPa with a mixture of cyclohexane and ethyl acetate (40/60 by volume) and 25 cc fractions being collected. Fractions 25 to 30 are combined and concentrated to dryness under reduced pressure (30 mm Hg; 4 kPa) at 40° C. This yields a hard yellow foam (0.030 g) consisting of a mixture (63/37 mols) of the E form of 2-benzhydryloxycarbonyl-3-(2-dimethylaminovinyl)-8-oxo-7-phenylacetamido-5-oxa-1-azabicyclo[4.2.0]oct-2-ene and the corresponding 3-(2-oxoethyl) derivative.

Physical characteristics of the E form of 2-benzhydryloxycarbonyl-3-(2-dimethylaminovinyl)-8-oxo-7-phenylacetamido-5-oxa-1-azabicyclo[4.2.0]oct-2-ene:

Mass spectrum: molecular peak=537.

Infra-red spectrum (KBr): characteristic bands (cm$^{-1}$): 3,430, 1,785, 1,725, 1,690, 1,620, 1,540, 1,500, 1,460, 1,440, 1,220, 1,180, 1,100, 760, 745, 705.

Proton NMR spectrum (350 MHz, CDCl$_3$, δ in ppm, J in Hz): 2.82 (s, 6H, —N(CH$_3$)$_2$); 3.65 (s, 2H, C$_6$H$_5$—CH$_2$—); 4.49 (d, J=16, 1H, —CH$_2$—O—); 4.62 (d, J=16, 1H, —CH$_2$—O—); 4.98 (d, J=3.5, 1H, —H in the 6-position); 5.62 (dd, J=9 and 3.5, 1H, —H in the 7-position); 6.28 (d, J=9, 1H, —CONH—); 6.31 (d, J=13.5, 1H, —CH=CH—); 6.45 (d, J=13.5, 1H, —CH=CH—); 6.85 (s, 1H, —COOCH(C$_6$H$_5$)$_2$); 7.10 to 7.60 (m, 15H, aromatic protons).

2-Benzhydryloxycarbonyl-3-methyl-8-oxo-7-phenylacetamido-5-oxa-1-azabicyclo[4.2.0]oct-2-ene can be obtained in the following manner:

A solution of phenylacetyl chloride (0.31 g) in anhydrous methylene chloride (1 cc) is added, in the course of 3 minutes, to a mixture of 7-amino-2-benzhydryloxycarbonyl-3-methyl-8-oxo-5-oxa-1-azabicyclo[4.2.0]oct-2-ene (0.73 g) and triethylamine (0.2 g) in anhydrous methylene chloride (20 cc), kept at −20° C. The mixture is stirred at this temperature for 15 minutes and then transferred into a separating funnel, in which the methylene chloride phase is washed successively with 0.1 N solution of hydrochloric acid (25 cc), a semi-saturated solution of sodium bicarbonate (25 cc) and distilled water (25 cc). It is dried over anhydrous magnesium sulphate. The magnesium sulphate is filtered off and washed with methylene chloride (5 cc) and the organic solutions are concentrated to dryness under reduced pressure (100 mm Hg; 13.5 kPa). This yields 2-benzhydryloxycarbonyl-3-methyl-8-oxo-7-phenylacetamido-5-oxa-1-azabicyclo[4.2.0]oct-2-ene (0.73 g) in the form of a hard white foam.

Mass spectrum: molecular peak=482.

Infra-red spectrum (KBr), characteristic bands (cm$^{-1}$): 3,420, 3,360, 1,790, 1,725, 1,685, 1,670, 1,540, 1,500, 1,460, 1,230, 750, 700.

Proton NMR spectrum (350 MHz, CDCl$_3$, δ in ppm, J in Hz): 1.99 (s, 3H, —CH$_3$); 3.66 (s, 2H, C$_6$H$_5$—CH$_2$—); 4.17 (d, J=17.5, 1H, —CH$_2$—O—); 4.25 (d, J=17.5, 1H, —CH$_2$—O—); 5.01 (d, J=3.5, 1H, —H in the 6-position); 5.68 (dd, J=10 and 3.5, 1H, —H in the 7-position); 6.16 (d, J=10, 1H, —CONH—); 6.88 (s, 1H, —COOCH(C$_6$H$_5$)$_2$); 7.13 to 7.60 (m, 15H, aromatic protons).

EXAMPLE 5

A solution of the E form of 2-benzhydryloxycarbonyl-3-(2-dimethylaminovinyl)-8-oxo-7-phenoxyacetamido-5-oxa-1-azabicyclo[4.2.0]oct-2-ene (0.09 g) in ethyl acetate (5 cc) is stirred vigorously for 30 minutes at 20° C., in the presence of a 1 N solution of hydrochloric acid (3 cc). The mixture is separated by decantation and the organic phase is washed with distilled water (10 cc), a 5% strength solution of sodium bicarbonate (10 cc), distilled water (10 cc) and then a semi-saturated solution of sodium chloride (10 cc). The ethyl acetate phase is dried over anhydrous magnesium sulphate and filtered and the filtrate is concentrated to dryness at 30° C. under reduced pressure (20 mm Hg; 2.7 kPa). This yields 2-benzhydryloxycarbonyl-3-(2-oxoethyl)-8-oxo-7-phenoxyacetamido-5-oxa-1-azabicyclo[4.2.0]oct-2-ene (0.07 g) in the form of a yellow resin.

Mass spectrum: molecular peak=526.

Infra-red spectrum (KBr), characteristic bands (cm$^{-1}$): 3,420, 2,930, 2,860, 2,730, 1,790, 1,720, 1,690, 1,670, 1,650, 1,530, 1,495, 1,455, 1,440, 1,240, 1,110, 1,070, 760, 700.

Proton NMR spectrum (350 MHz, CDCl$_3$, δ in ppm, J in Hz): 3.52 (d, J=17.5, 1H, —CH$_2$—CHO); 3.63 (d, J=17.5, 1H, —CH$_2$—CHO); 4.32 (d, J=17.5, 1H, —CH$_2$—O—); 4.40 (d, J=17.5, 1H, —CH$_2$—O—); 4.58 (s, 2H, C$_6$H$_5$O—CH$_2$—); 5.15 (d, J=3.5, 1H, —H in the 6-position); 5.80 (dd, J=10 and 3.5, 1H, —H in the 7-position); 6.88 (s, 1H, —COOCH(C$_6$H$_5$)$_2$); 6.9 to 7.60 (m, 16H, aromatic protons and —CONH—); 9.60 (s, 1H, —CHO).

The E form of 2-benzhydryloxycarbonyl-3-(2-dimethylaminovinyl)-8-oxo-7-phenoxyacetamido-5-oxa-1-azabicyclo[4.2.0]oct-2-ene can be obtained in the following manner:

A solution of 2-benzhydryloxycarbonyl-3-methyl-8-oxo-7-phenoxyacetmido-5-oxa-1-azabicyclo[4.2.0]oct-2-ene (0.86 g) in dimethylformamide (13 cc) is heated to 80° C. under nitrogen. t-Butoxy-bis-dimethylaminomethane (0.44 cc) is added dropwise, in the course of 2 minutes, to the solution stirred at 80° C. When the addition has ended, the mixture is stirred at 80° C. for 20 minutes. The solution is diluted with ethyl acetate (100 cc), the organic phase is washed with distilled water (3×50 cc) and a saturated solution of sodium chloride (50 cc), dried over magnesium sulphate and filtered and the filtrate is concentrated to dryness at 40° C. under reduced pressure (20 mm Hg; 2.7 kPa). This yields a crude product (0.93 g) consisting mainly of the E form of 2-benzhydryloxycarbonyl-3-(2-dimethylaminovinyl)-8-oxo-7-phenoxyacetamido-5-oxa-1-azabicyclo[4.2.0]oct-2-ene.

This product (0.90 g) is purified by chromatography on a column of silica (0.04–0.06) (diameter of the column: 3.8 cm; height: 23 cm), elution being carried out under 50 kPa with a mixture of cyclohexane and ethyl acetate (40/60 by volume) and 40 cc fractions being collected. Fractions 9 to 13 are combined and concentrated to dryness under reduced pressure (30 mm Hg; 4 kPa) at 40° C. This yields a hard orange-yellow foam (0.12 g) of the pure product.

Infra-red spectrum (KBr), characteristic bands (cm$^{-1}$): 3,420, 1,785, 1,720, 1,690, 1,615, 1,600, 1,590, 1,525, 1,495, 1,455, 1,440, 1,240, 1,105, 1,070, 765.

Proton NMR spectrum (250 MHz, CDCl$_3$, δ in ppm, J in Hz): 2.86 (s, 6H, —N(CH$_3$)$_2$); 4.56 (AB-type, J=14, 2H, C$_6$H$_5$—O—CH$_2$—); 4.60 (d, J=16, 1H, —O—CH$_2$—); 4.79 (d, J=16, 1H, —O—CH$_2$—); 5.08 (d, J=4, 1H, H in the 6-position); 5.70 (dd, J=9 and 4, 1H, —H in the 7-position); 6.36 (d, J=14, 1H, —CH═CH—); 6.54 (d, J=14, 1H, —CH═CH—); 6.88 (s, 1H, —COOCH(C$_6$H$_5$)$_2$); 6.93 (d, J=7.5, 2H, C$_6$H$_5$—O—CH$_2$—, H in the ortho-position); 7.03 (t, J=7.5, 1H, C$_6$H$_5$OCH$_2$—, H in the para-position); 7.10 to 7.70 (m, aromatic protons and —CONH—).

2-Benzhydryloxycarbonyl-3-methyl-8-oxo-7-phenoxyacetamido-5-oxa-1-azabicyclo[4.2.0]oct-2-ene can be prepared in the following manner:

A solution of phenoxyacetyl chloride (1.71 g) in anhydrous methylene chloride (5 cc) is added, in the course of 15 minutes, to a mixture of 7-amino-2-benzhydryloxycarbonyl-3-methyl-8-oxo-5-oxa-1-azabicyclo[4.2.0]oct-2-ene (3.64 g) and triethylamine (1.01 g) in anhydrous methylene chloride (50 cc), kept at −20° C. The mixture is stirred at this temperature for 15 minutes, the cooling bath is then removed and the temperature of the mixture is allowed to rise to about 20° C. The mixture is washed successively with a 0.1 N solution of hydrochloric acid (50 cc), distilled water (50 cc), a semi-saturated solution of sodium bicarbonate (50 cc), distilled water (50 cc) and a semi-saturated solution of sodium chloride (50 cc). The methylene chloride solution is then dried over anhydrous magnesium sulphate and filtered and the filtrate is concentrated to dryness under reduced pressure (100 mm Hg; 13.5 kPa). This yields a residue (4.73 g) in the form of a hard foam consisting of 2-benzhydryloxycarbonyl-3-methyl-8-oxo-7-phenoxyacetamido-5-oxa-1-azabicyclo[4.2.0]oct-2-ene.

Mass spectrum: molecular peak=498.

Infra-red spectrum (KBr), characteristic bands (cm$^{-1}$): 3,420, 3,350, 1,790, 1,720, 1,690, 1,640, 1,600, 1,590, 1,530, 1,495, 1,490, 1,455, 1,440, 1,230, 1,110, 1,065, 755, 700.

Proton NMR spectrum (350 MHz, CDCl$_3$, δ in ppm, J in Hz): 2.04 (s, 3H, —CH$_3$); 4.34 (s, 2H, —CH$_2$O—); 4.58 (s, 2H, C$_6$H$_5$O—CH$_2$—); 5.11 (d, J=3.5, 1H, —H in the 6-position); 5.75 (dd, J=10.5 and 3.5, 1H, —H in the 7-position); 6.92 (s, 1H, —COOCH(C$_6$H$_5$)$_2$); 6.94 (d, J=7.5, 2H, C$_6$H$_5$O— (H in the ortho-position)); 7.04 (t, J=7.5, 1H, C$_6$H$_5$O— (H in the para-position)); 7.20 to 7.60 (m, 13H, aromatic protons and —CO—NH—).

EXAMPLE 6

A solution of the E form of 2-benzhydryloxycarbonyl-3-(2-dimethylaminovinyl)-7α-methoxy-8-oxo-7-phenoxyacetamido-5-oxa-1-azabicyclo[4.2.0]oct-2-ene (0.010 g) in ethyl acetate (5 cc) is stirred vigorously for 30 minutes at 20° C., in the presence of a 1 N solution of hydrochloric acid (3 cc). The mixture is separated by decantation and the organic phase is washed with distilled water (10 cc), a saturated solution of sodium bicarbonate (10 cc), distilled water (10 cc) and a saturated solution of sodium chloride (10 cc). The ethyl acetate phase is dried over anhydrous magnesium sulphate and filtered and the filtrate is concentrated to dryness at 30° C. under reduced pressure (20 mm Hg; 2.7 kPa). This yields 2-benzhydryloxycarbonyl-7α-methoxy-3-(2-oxoethyl)-8-oxo-7-phenoxyacetamido-5-oxa-1-azabicyclo[4.2.0]oct-2-ene (0.009 g) in the form of a hard, light chestnut-coloured foam.

Mass spectrum: molecular peak=556.

Proton NMR spectrum (350 MHz, CDCl$_3$, δ in ppm, J in Hz): 3.50 (s, —OCH$_3$); 4.25 (s, —O—CH$_2$—); 4.50 (s, C$_6$H$_5$O—CH$_2$—); 5.08 (s, H$_6$); 6.79 (s, —COOCH(C$_6$H$_5$)$_2$); 9.48 (s, —CHO).

The E form of 2-benzhydryloxycarbonyl-3-(2-dimethylaminovinyl)-7α-methoxy-8-oxo-7-phenoxyacetamido-5-oxa-1-azabicyclo[4.2.0]oct-2-ene can be obtained in the following manner:

A solution of 2-benzhydryloxycarbonyl-7α-methoxy-3-methyl-8-oxo-7-phenoxyacetamido-5-oxa-1-azabicyclo-[4.2.0]oct-2-ene (1.5 g) in dimethylformamide (0.7 cc) is heated to 80° C. under nitrogen. t-Butoxycarbonyl-bis-dimethylaminomethane (0.7 cc) is added dropwise, in the course of 5 minutes, to the solution stirred at 80° C. When the addition has ended, the mixture is stirred at 80° C. for 30 minutes. The solution is diluted with ethyl acetate (100 cc), the organic phase is washed with distilled water (6×100 cc) and a saturated solution of sodium chloride (100 cc), dried over magnesium sulphate and filtered and the filtrate is concentrated to dryness under reduced pressure (20 mm Hg; 2.7 kPa) at 40° C. This yields a crude product (1.19 g) consisting mainly of the E form of 2-benzhydryloxycarbonyl-3-(2-dimethylaminovinyl)-7α-methoxy-8-oxo-7-phenoxyacetamido-5-oxa-1-azabicyclo[4.2.0]oct-2-ene.

Mass spectrum: molecular peak=583.

Infra-red spectrum (KBr), characteristic bands (cm$^{-1}$): 1,775, 1,700, 1,615, 1,495, 1,460, 1,440, 760, 700.

Proton NMR spectrum (350 MHz, CDCl$_3$, δ in ppm, J in Hz): 2.85 (s, 6H, —N(CH$_3$)$_2$); 3.58 (s, 3H, CH$_3$O—); 4.57 (s, 2H, —O—CH$_2$—); 4.63 (s, 2H, C$_6$H$_5$OCH$_2$—); 5.14 (s, 1H, —H in the 6-position); 6.30 (d, J=14, 1H, —CH═CH—); 6.53 (d, J=14, 1H, —CH═CH—); 6.88 (s, 1H, —COOCH(CH$_6$H$_5$)$_2$); 6.9 to 7.6 (m, 15H, aromatic protons).

2-Benzhydryloxycarbonyl-7α-methoxy-3-methyl-8-oxo-7-phenoxyacetamido-5-oxa-1-azabicyclo[4.2.0]oct-2-ene can be obtained in the following manner:

A 1.6 N solution of n-butyllithium in hexane (13 cc) is added to dry tetrahydrofuran (50 cc) cooled to −40° C. and kept under nitrogen. Anhydrous methanol (3 cc) is added slowly, the mixture is then cooled to −74° C. and a solution of 2-benzhydryloxycarbonyl-3-methyl-8-oxo-7-phenoxyacetamido-5-oxa-1-azabicyclo-[4.2.0]oct-2-ene (3 g) in tetrahydrofuran (14 cc) is added. The solution obtained is kept at −74° C. for 3 minutes and t-butyl hypochlorite (0.84 cc) is added. The mixture is stirred at −74° C. for 1 hour 20 minutes and a mixture of glacial acetic acid and triethyl phosphite (50/50 by volume) (2 cc) is then poured in as a fine stream. The temperature of the reaction mixture is allowed to rise to about 20° C. and the mixture is diluted with ethyl acetate (100 cc). The organic phase is washed successively with a 5% strength solution of sodium bicarbonate (100 cc), distilled water (100 cc) and a saturated solution of sodium chloride (100 cc), dried over anhydrous magnesium sulphate and filtered and the solvent is evaporated off under 20 mm Hg (2.7 kPa). The residue is purified by chromatography on silica gel (0.04–0.06) (diameter of the column: 4.2 cm; height of silica: 24 cm), elution being carried out with a mixture of cyclohexane and ethyl acetate (55/45 by volume) under a pressure of 40 kPa and 50 cc fractions being collected. Fractions 10 to 17 are concentrated to dryness under reduced pressure (30 mm Hg; 4 kPa) at 30° C. This yields 2-benzhydryloxycarbonyl-7α-methoxy-3-methyl-8-oxo-7-phenoxyacetamido-5-oxa-1-azabicyclo[4.2.0]oct-2-ene (1.55 g) in the form of a hard white foam.

Mass spectrum: molecular peak = 528.

Infra-red spectrum (CHBr$_3$), characteristic bands (cm$^{-1}$): 3,410, 1,780, 1,710, 1,645, 1,600, 1,590, 1,500, 1,460, 1,440, 1,230, 1,080, 760.

Proton NMR spectrum (350 MHz, CDCl$_3$, δ in ppm, J in Hz): 2.02 (s, 3H, —CH$_3$); 3.58 (s, 3H, —OCH$_3$); 4.27 (d, J=17.5, 1H, —OCH$_2$—); 4.34 (d, J=17.5, 1H, —O—CH$_2$—); 4.58 (s, 2H, C$_6$H$_5$—O—CH$_2$—); 5.14 (s, 1H, —H in the 6-position); 6.92 (s, 1H, —COOCH(C$_6$H$_5$)$_2$); 6.96 (d, J=7, 2H, C$_6$H$_5$—O—, H in the ortho-position); 7.05 (t, J=7, 1H, H in the para-position of the C$_6$H$_5$O—); 7.15 to 7.60 (m, aromatic protons +—CONH—).

EXAMPLE 7

A solution of the E form of 3-(2-dimethylaminovinyl)-2-p-nitrobenzyloxycarbonyl-8-oxo-7-tritylamino-5-oxa-1-azabicyclo[4.2.0]oct-2-ene (obtained as described below) (0.016 g) in ethyl acetate (5 cc) is stirred vigorously for 30 minutes at 20° C., in the presence of a 1 N solution of hydrochloric acid (5 cc). The mixture is separated by decantation and the organic phase is washed with a semi-saturated solution of sodium bicarbonate (2×5 cc) and then with a semi-saturated solution of sodium chloride (2×5 cc). The ethyl acetate phase is dried over anhydrous sodium sulphate and filtered and the filtrate is concentrated to dryness at 30° C. under reduced pressure (20 mm Hg; 2.7 kPa). This yields 2-p-nitrobenzyloxycarbonyl-3-(2-oxoethyl)-8-oxo-7-tritylamino-5-oxa-1-azabicyclo[4.2.0]oct-2-ene (0.012g) in the form of a hard, light chestnut-coloured foam.

Proton NMR spectrum (250 MHz, CDCl$_3$, δ in ppm, J in Hz): 3.44 (d, J=16.25, 1H, —CH$_2$—CHO); 3.57 (d, J=16.25, 1H, —CH$_2$—CHO); 3.84 (d, J=3.75, 1H, —H in the 6-position); 3.96 (d, J=18.75, 1H, —CH$_2$—O—); 4.17 (d, J=18.75, 1H, —CH$_2$O—); 4.34 (dd, J=9 and 3.75, 1H, —H in the 7-position); 5.21 (d, J=12.0, 1H, —CH$_2$C$_6$H$_4$NO$_2$); 5.37 (d, J=12.0, 1H, —CH$_2$C$_6$H$_4$NO$_2$); 7.10 to 7.75 (m, 18H, aromatic protons and (C$_6$H$_5$)$_3$C—NH—); 8.23 (d, J=8, 2H, aromatic protons in the ortho-positions to the nitro); 9.56 (s, 1H, —CHO).

The E form of 3-(2-dimethylaminovinyl)-2-p-nitrobenzyloxycarbonyl-8-oxo-7-tritylamino-5-oxa-1-azabicyclo-[4.2.0]oct-2-ene can be obtained in the following manner:

A solution of 3-methyl-2-p-nitrobenzyloxycarbonyl-8-oxo-7-tritylamino-5-oxa-1-azabicyclo[4.2.0]oct-2-ene (0.58 g) in dry dioxane (10 cc) is heated to 70° C. under nitrogen. A solution of t-butoxy-bis-dimethylaminomethane (0.5 cc) in dry dioxane (2 cc) is added dropwise in the course of 10 minutes. When the addition has ended, the mixture is stirred at 70° C. for 20 minutes. The solution is diluted with ethyl acetate (100 cc), the organic phase is washed with a semi-saturated solution of sodium chloride (6×100 cc), dried over sodium sulphate and filtered and the filtrate is concentrated to dryness at 40° C. under reduced pressure (20 mm Hg; 2.7 kPa). This yields a crude product (0.2 g), which is purified by chromatography on a column of silica (0.04–0.06) (diameter of the column: 2.1 cm; height: 20 cm), elution being carried out under 50 kPa with a mixture of cyclohexane and ethyl acetate (60/40 by volume) and 15 cc fractions being collected. Fraction 9 is concentrated to dryness under reduced pressure (30 mm Hg; 4 kPa) at 40° C. This yields a yellow powder (0.02 g) consisting of a mixture of the E form of 3-(2-dimethylaminovinyl)-2-p-nitrobenzyloxycarbonyl-8-oxo-7-tritylamino-5-oxa-1-azabicyclo[4.2.0]oct-2-ene and the corresponding 3-(2-oxoethyl) derivative.

Proton NMR spectrum (250 MHz, CDCl$_3$, δ in ppm, J in Hz): 2.83 (s, 6H, —N(CH$_3$)$_2$); 3.75 (d, J=3, 1H, —H in the 6-position); 4.21 (d, J=15.5, 1H, —O—CH$_2$—); 4.43 (dd, J=9 and 3, 1H, —H in the 7-position); 4.56 (d, J=15.5, 1H, —O—CH$_2$—); 5.18 (d, J=12.0, 1H, —CH$_2$—C$_6$H$_4$NO$_2$); 5.41 (d, J=12.0, 1H, —CH$_2$—C$_6$H$_4$NO$_2$); 6.21 (d, J=13.75, 1H, —CH=CH—); 6.48 (d, J=13.75, 1H, —CH=CH—); 7.10 to 7.75 (m, 18H, aromatic protons and (C$_6$H$_5$)$_3$C—NH—); 8.20 (d, J=8, 2H, aromatic protons in the ortho-positions to the nitro).

REFERENCE EXAMPLE 1

2-Benzhydryloxycarbonyl-3-(2-oxoethyl)-8-oxo-7-tritylamino-5-oxa-1-azabicyclo[4.2.0]oct-2-ene (2.51 g) is dissolved in pyridine (20 cc). Tosyl chloride (1.13 g) is added to the solution obtained and the mixture is stirred at 20° C. for 1 hour 25 minutes. The solution is poured into iced water (150 cc), a gum deposits on the walls of the container, the aqueous phase is decanted and the gummy substance is dissolved in ethyl acetate (45 cc). The organic solution is washed with a 0.1 N solution of hydrochloric acid (2×50 cc), a 5% strength solution of sodium bicarbonate (50 cc) and a semi-saturated solution of sodium chloride (30 cc), dried over sodium sulphate and filtered and the filtrate is concentrated to dryness at 30° C. under reduced pressure (20 mm Hg; 2.7 kPa). A chestnut-coloured crude product (2.4 g), consisting essentially of a mixture of the E and Z forms of 2-benzhydryloxycarbonyl-8-oxo-3-(2-tosyloxyvinyl)-7-tritylamino-5-oxa-1-azabicyclo[4.2.0]oct-2-ene, is collected.

Infra-red spectrum (KBr), characteristic bands (cm$^{-1}$): 1,790, 1,725, 1,595, 1,490, 1,450, 1,380, 1,190, 1,180, 745, 700.

The sodium salt of 5-mercapto-2-methyl-1,3,4-thiadiazole (0.28 g) is added to a solution of a mixture of the E and Z forms of 2-benzhydryloxycarbonyl-8-oxo-3-(2-tosyloxyvinyl)-7-tritylamino-5-oxa-1-azabicyclo[4.2.0]-oct-2-ene (2.4 g) in dimethylformamide (15 cc). The mixture is stirred at 20° C. for 2 hours and then diluted with ethyl acetate (50 cc). The solution is washed with distilled water (5×50 cc) and a semi-saturated solution of sodium chloride (50 cc) and then dried over sodium sulphate. The mixture is filtered and the filtrate is concentrated to dryness at 20° C. under reduced pressure (20 mm Hg; 2.7 kPa). The residue (2.1 g) is chromatographed on a column of Merck silica gel (0.04–0.06) (diameter of the column: 4.1 cm; height: 20 cm). Elution is carried out with a 70/30 (by volume) cyclohexane/ethyl acetate mixture (1 liter) under a pressure of 50 kPa, 60 cc fractions being collected. Fractions 9 and 10 are concentrated to dryness under reduced pressure (30 mm Hg; 4 kPa) at 30° C. This yields the E form of 2-benzhydryloxycarbonyl-3-[2-(2-methyl-1,3,4-thiadiazol-5-yl)-thiovinyl]-8-oxo-7-tritylamino-5-oxa-1-azabicyclo[4.2.0]oct-2-ene (0.13 g) in the form of a hard, pale yellow foam.

Infra-red spectrum (KBr), characteristic bands (cm$^{-1}$): 1,790, 1,720, 1,490, 1,450, 1,210, 745, 700.

Proton NMR spectrum (350 MHz, CDCl$_3$, δ in ppm, J in Hz): 2.74 (s, 3H, —CH$_3$), 3.76 (d, J=3.5, 1H, H in the 6-position); 4.16 and 4.62 (2d, J=18, 2H, —CH$_2$—O—); 4.37 (d, J=3.5, 1H, H in the 7-position); 6.84 (s, 1H, —COO—CH(C$_6$H$_5$)$_2$); 6.96 (d, J=17, 1H, —CH=CH—S—).

The E form of 2-benzhydryloxycarbonyl-3-[2-(2-methyl-1,3,4-thiadiazol-5-yl)-thiovinyl]-8-oxo-7-tritylamino-5-oxa-1-azabicyclo[4.2.0]oct-2-ene (0.112 g) is dissolved in acetone (1.4 cc), and p-toluenesulphonic acid monohydrate (0.029 g) is added to the solution. The solution is heated under reflux for 45 minutes, during which time crystals develop on the walls of the container. The suspension is filtered and the filtrate is poured into a 1% strength solution of sodium bicarbonate (10 cc). The mixture is extracted with ethyl acetate (2×5 cc), the organic phase is dried over sodium sulphate and filtered and the filtrate is concentrated to dryness at 30° C. under reduced pressure (20 mm Hg; 2.7 kPa). A chestnut-coloured crude solid (0.1 g), consisting essentially of the E form of 7-amino-2-benzhydryloxycarbonyl-3-[2-(2-methyl-1,3,4-thiadiazol-5-yl)-thiovinyl]-8-oxo-5-oxa-1-azabicyclo[4.2.0]oct-2-ene, is thus collected.

Rf=0.20 [silica gel chromatography plate, eluent: 80/20 (by volume) cyclohexane/ethyl acetate].

The syn isomer of 2-methoxyimino-2-(2-tritylaminothiazol-4-yl)-acetic acid (0.089 g), N,N'-dicyclohexylcarbodiimide (0.041 g) and 4-N,N-dimethylaminopyridine (0.001 g) are added to a solution of the E form of 7-amino-2-benzhydryloxycarbonyl-3-[2-(2-methyl-1,3,4-thiadiazol-5-yl)-thiovinyl]-8-oxo-5-oxa-1-azabicyclo[4.2.0]oct-2-ene (0.1 g) in methylene chloride (20 cc). The mixture is stirred at 20° C. for 1 hour 30 minutes. Acetic acid (0.1 cc) is then added; a small amount of insoluble material is removed by filtration, the filtrate is concentrated to dryness at 30° C. under reduced pressure (100 mm Hg; 13.3 kPa) and the residue is dissolved in ethyl acetate (5 cc). The solution is washed with 0.1 N hydrochloric acid (2×2.5 cc) and then with a 1% strength solution of sodium bicarbonate (5 cc) and distilled water (5 cc). It is dried over sodium sulphate and filtered and the filtrate is concentrated to dryness at 30° C. under 20 mm Hg (2.7 kPa). The residue (0.12 g) is fixed onto Merck silica gel (0.05–0.2) (0.25 g) and the powder obtained is deposited on a column of silica gel (10 g) (diameter of the column: 1 cm). Elution is carried out successively with a 50/50 (by volume) cyclohexane/ethyl acetate mixture (70 cc), a 40/60 mixture (30 cc) and a 20/80 mixture (30 cc), 2.5 cc fractions being collected. Fractions 22 to 40 are concentrated to dryness at 20° C. under reduced pressure (20 mm Hg; 2.7 kPa) and the E form of the syn isomer of 2-benzhydryloxycarbonyl-7-[2-methoxyimino-2-(2-tritylaminothiazol-4-yl)-acetamido]-3-[2-(2-methyl-1,3,4-thiadiazol-5-yl)-thiovinyl]-8-oxo-5-oxa-1-azabicyclo[4.2.0]oct-2-ene (0.023 g) is collected in the form of a hard orange foam.

Infra-red spectrum (KBr), characteristic bands (cm$^{-1}$): 1,795, 1,720, 1,685, 1,520, 1,495, 1,450, 1,210, 1,045, 750, 700.

Proton NMR spectrum (350 MHz, CDCl$_3$, δ in ppm, J in Hz): 2.74 (s, 3H, —CH$_3$); 4.07 (s, 3H, =N—O—CH$_3$); 4.59 and 4.86 (2d, J=18, 2H, —CH$_2$—O—); 5.13 (d, J=3.5, 1H, —H in the 6-position); 5.81 (dd, J=3.5 and 9, 1H, —H in the 7-position); 6.78 (s, 1H, —H of the thiazole); 6.79 (d, J=9, 1H, —CO—NH—); 6.88 (s, 1H, —COO—CH(C$_6$H$_5$)$_2$); 7.03 (m, 1H, —NH—C(C$_6$H$_5$)$_3$); 7.14 and 7.69 (2d, J=17, 2H, —CH=CH—S—).

Distilled water (0.5 cc) is added to a solution of the E form of the syn isomer of 2-benzhydryloxycarbonyl-7-[2-methoxyimino-2-(2-tritylaminothiazol-4-yl)-acetamido]-3-[2-(2-methyl-1,3,4-thiadiazol-5-yl)-thiovinyl]-8-oxo-5-oxa-1-azabicyclo[4.2.0]oct-2-ene (0.023 g) in formic acid (1 cc) and the mixture is heated at 50° C. for 20 minutes, whilst stirring. After cooling, the insoluble material is filtered off and the filtrate is concentrated to dryness at 30° C. under reduced pressure (20 mm Hg; 2.7 kPa). The residue is taken up in ethanol (2×15 cc), each solution being concentrated to dryness at 20° C. under 20 mm Hg (2.7 kPa), and the residue is triturated in ethyl ether (20 cc). After filtration, the E form of the syn isomer of 7-[2-(2-aminothiazol-4-yl)-2-methoxyiminoacetamido]-2-carboxy-3-[2-(2-methyl-1,3,4-thiadiazol-5-yl)-thiovinyl]-8-oxo-5-oxa-1-azabicyclo[4.2.0]oct-2-ene (0.010 g) is obtained in the form of a yellow powder.

Infra-red spectrum (KBr), characteristic bands (cm$^{-1}$): 1.785, 1,670, 1,620, 1,530, 1,040.

Proton NMR spectrum (350 MHz, d$_6$—DMSO, δ in ppm, J in Hz): 2.70 (s, —CH$_3$); 3.83 (s, =N—OCH$_3$); 4.50 and 4.78 (2d, J=18, —CH$_2$—O—); 5.14 (d, J=3.5, —H in the 6-position); 5.45 (m, —H in the 7-position); 6.75 (s, —H of the thiazole); 7.10 to 7.70 (m, —NH$_2$ and —CH=CH—S—); 9.34 (d, J=9, —CO—NH).

REFERENCE EXAMPLE 2

The product of Example 2 can be used in the following manner:

Triethylamine (0.27 cc) is added, in the course of 10 minutes, to a solution, cooled to −5° C., of the syn isomer of 2-benzhydryloxycarbonyl-7-[2-methoxyimino-2-(2-tritylaminothiazol-4-yl)-acetamido]-8-oxo-3-(2-oxoethyl)-5-oxa-1-azabicyclo[4.2.0]oct-2-ene (1.00 g) and tosyl chloride (0.35 g) in methylene chloride (20 cc). The mixture is stirred at −5° C. for 10 minutes and then left to return to 20° C. The mixture is then stirred for 30 minutes. The solvent is evaporated off under reduced pressure (350 mm Hg; 47 kPa). This yields a chestnut-coloured oil, which solidifies on stirring with ether (100 cc). The solid is filtered off and dried. This yields the E form of the syn isomer of 2-benzhydryloxycarbonyl-7-[2-methoxyimino-2-(2-tritylaminothiazol-4-yl)acetamido]-8-oxo-3-(2-tosyloxyvinyl)-5-oxa-1-azabicyclo[4.2.0]oct-2-ene (0.38 g) in the form of a cream-coloured powder. The filtrate is concentrated to a residual volume of 5 cc and isopropyl ether (100 cc) is added. A pale yellow solid separates out. It is isolated on a filter and a second fraction of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-oxa-1-azabicyclo[4.2.0]oct-2-ene (0.11 g) is obtained.

Infra-red spectrum (KBr), characteristic bands (cm$^{-1}$): 3,400, 1,800, 1,720, 1,685, 1,600, 1,520, 1,495, 1,450, 1,380, 1,195, 1,180, 1,070, 815, 755, 700.

Proton NMR spectrum (250 MHz, CDCl$_3$, δ in ppm, J in Hz): 2.44 (s, 3H, CH$_3$ of the tosyl); 4.08 (s, 3H, =NOCH$_3$); 4.44 (d, J=16.25, 1H, —O—CH$_2$—); 4.64 (d, J=16.25, 1H, —O—CH$_2$—); 5.12 (d, J=3.75, 1H, —H in the 6-position); 5.79 (dd, J=8 and 3.75, —1H, —H in the 7-position); 6.72 (d, J=8, 1H, —CONH—); 6.77 (s, 1H, —H of the thiazole); 6.82 (d, J=12.5, 1H, —CH=CH—); 6.83 (s, 1H, —COOCH(C$_6$H$_5$)$_2$); 7.03 (m, 1H, C$_6$H$_5$)$_3$CNH—); 7.17 (d, J=12.5, 1H, —CH=CH—); 7.20 to 7.55 (m, 27H, aromatic protons); 7.75 (d, J=8, 2H in the orthopositions of the tosyl).

A solution of the E form of the syn isomer of 2-benzhydryloxycarbonyl-7-[2-methoxyimino-2-(2-tritylaminothiazol-4-yl)-acetamido]-8-oxo-3-(2-tosyloxyvinyl)-5-oxa-1-azabicyclo[4.2.0]oct-2-ene (0.53 g) and sodium [4-(2,2-dimethoxyethyl)-1,4,5,6-tetrahydro-5,6-dioxo-1,2,4-triazin-3-yl]-thiolate (0.139 g) in dimethylformamide (12 cc) is heated at 40° C. for 6 hours, whilst stirring. The mixture is transferred into a separating funnel containing ethyl acetate (30 cc) and distilled water (50 cc). After decantation, the organic phase is washed with distilled water (3×50 cc) and then dried over anhydrous magnesium sulphate. The solvent is evaporated off under reduced pressure (20 mm Hg; 2.7 kPa) and the residue (0.52 g) is purified by chromatography on a column of Merck silica gel (0.04–0.06) (diameter of the column: 2.2 cm; height: 25.5 cm). Elution is carried out with a 15/85 (by volume) cyclohexane/ethyl acetate mixture under a pressure of 50 kPa, 20 cc fractions being collected. Fractions 10 to 28 are concentrated to dryness under reduced pressure (30 mm Hg; 4 kPa) at 30° C. This yields the E form of the syn isomer of 2-benzhydryloxycarbonyl-3-[[2-[4-(2,2-dimethoxyethyl)-1,4,5,6-tetrahydro-5,6-dioxo-1,2,4-triazin-3-yl]-thiovinyl]]-7-[2-methoxyimino-2-(2-tritylaminothiazol-4-yl)-acetamido]-8-oxo-5-oxa-1-azabicyclo[4.2.0]oct-2-ene (0.20 g) in the form of a hard, light chestnut-coloured foam.

Proton NMR spectrum (250 MHz, CDCl$_3$, δ in ppm, J in Hz): 3.42 (s, 6H, (—OCH$_3$)$_2$); 4.03 (limiting AB-type, J=4.5 and 10, 2H, >NCH$_2$—); 4.06 (s, 3H, =N—OCH$_3$); 4.58 (d, J=16.25, 1H, —OCH$_2$—); 4.65 (t, J=5, 1H, —CH(OCH$_3$)$_2$); 4.84 (d, J=16.25, 1H, —O—CH$_2$—); 5.15 (d, J=3.15, 1H, —H in the 6-position); 5.81 (dd, J=10 and 3.15, 1H, —H in the 7-position); 6.73 (d, J=16.25, 1H, —CH=CH—); 6.79 (s, 1H, —H of the thiazole); 6.87 (s, 1H, —COOCH(C$_6$H$_5$)$_2$); 7.05 (m, 1H, (C$_6$H$_5$)$_3$CNH—); 7.18 (d, J=10, 1H, —CONH—); 7.20 to 7.55 (m, 25H, aromatic protons); 7.68 (d, J=16.25, 1H, —CH=CH—); 10.09 (s broad, 1H, —NH— of the triazine).

p-Toluenesulphonic acid monohydrate (0.74 g) is added to a solution of the E form of the syn isomer of 2-benzhydryloxycarbonyl-3-[[2-[4-(2,2-dimethoxyethyl)-1,4,5,6-tetrahydro-5,6-dioxo-1,2,4-triazin-3-yl]-thiovinyl]]-7-[2-methoxyimino-2-(2-tritylaminothiazol-4-yl)-acetamido]-8-oxo-5-oxa-1-azabicyclo[4.2.0]oct-2-ene (0.20 g) in acetonitrile (5 cc) at 50° C. The mixture is kept at this temperature for 30 minutes. After cooling to 20° C., the precipitate which has developed during the reaction is filtered off.

It is washed with acetonitrile (1 cc) and then stirred vigorously in distilled water (5 cc) for 30 minutes. The suspension is filtered and the chestnut-coloured powder obtained is dried under reduced pressure (10 mm Hg; 1.33 kPa) to give the E form of the syn isomer of 7-[2-(2-aminothiazol-4-yl)-2-methoxyiminoacetamido]-2-carboxy-3-[[2-[1,4,5,6-tetrahydro-5,6-dioxo-4-(2-oxoethyl)-1,2,4-triazin-3-yl]-thiovinyl]]-8-oxo-5-oxa-1-azabicyclo[4.2.0]oct-2-ene tosylate (20 mg).

Proton NMR spectrum (250 MHz, CF$_3$CO$_2$D, δ in ppm, J in Hz): 2.47 (s, 3H, —CH$_3$); 4.30 (s, 3H, =NOCH$_3$); 5.17 (m, >NCH$_2$—); 5.45 (m, 1H, —H in the 6-position); 5.91 (m, 1H, —H in the 7-position); 7.39 (d, J=8, 2H, H of the tosyl); 7.53 (s, 1H, —H of the thiazole); 7.82 (d, J=8, 2H, H of the tosyl); 9.76 (s, 1H, —CHO).

We claim:

1. A new oxacephalosporin of the general formula:

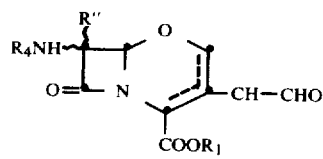

which is in the form of a bicyclooct-2-ene or bicyclooct-3-ene or a 3-oxoethylidenebicyclooctane and in which the symbol R$_1$ represents a protective radical and
   (a) the symbol R$_4$ represents a radical of the general formula:

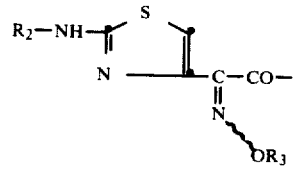

in which R$_2$ is an amino-protecting radical and R$_3$ is a hydrogen atom, an oxime-protecting radical, an alkyl or vinyl radical or a carboxyalkyl radical represented by the general formula:

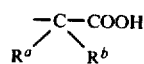

in which the radicals R$^a$ and R$^b$, which are identical or different, represent hydrogen atoms or alkyl radicals, or together form an alkylene radical containing 2 or 3 carbon atoms, and of which the acid group can be protected; or R$_4$ represents a free or protected α-carboxyarylacetyl radical in which aryl represents phenyl, free or protected p-hydroxyphenyl, or thien-2-yl or thien-3-yl, and the symbol R″ represents a hydrogen atom or a methoxy radical in the 7α-position, or alternatively
   (b) the symbol R$_4$ represents a radical which can easily be removed chosen from amongst:
   (1) benzhydryl or trityl,
   (2) an acyl radical of the formula:

R$_5$CO— in which R$_5$ represents:
(a) hydrogen, alkyl of 1 to 7 carbon atoms, methyl substituted by 1 to 3 halogen atoms, alkenyl of 3 to 7 carbon atoms or cyanomethyl,
(b) phenyl which is unsubstituted or substituted by one to three substituents selected from halogen, hydroxy, nitro, cyano, trifluoromethyl, alkyl and alkoxy, or thien-2-yl or thien-3-yl,
(c) a radical of the formula:

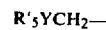

in which R'$_5$ represents a radical as defined under (b) and Y is sulphur or oxygen, or
(d) an arylalkyl radical of the formula:

in which R″$_5$ represents a phenyl radical which is unsubstituted or substituted by one to three substituents selected from hydroxyl, alkyl and alkoxy or thien-2-yl, thien-3-yl, furan-2-yl, furan-3-yl, or tetrazol-1-yl, (3) a radical of the formula:

in which R₆ is unsubstituted branched alkyl, linear or branched alkyl substituted by halogen, cyano, phenyl, or phenyl substituted by halogen, alkyl, alkoxy, nitro or phenyl, 2-trimethylsilylethyl, vinyl, allyl, or quinolyl, (4) a radical of the formula:

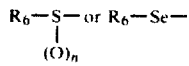

in which formulae R₆ is alkyl, phenyl, or phenyl substituted by halogen, nitro or alkyl, and n is 0 to 1, or (5) a bis-(4-nitrobenzyl)-phosphoryl radical, or (6) R₄NH— is replaced by alkylaminomethyleneamino or by a radical of the formula:

in which Ar is phenyl unsubstituted or substituted by alkoxy, nitro, alkyl or hydroxyl, and the symbol R'' represents a hydrogen atom or a methoxy radical in the 7α-position or a hydrogen atom in the 7β-position, it being understood that the abovementioned alkyl or acyl radicals and portions are linear or branched, unless otherwise mentioned, and contain 1 to 4 carbon atoms, if appropriate in its syn or anti forms.

2. A new product according to claim 1, in which R₄ represents a radical of the general formula:

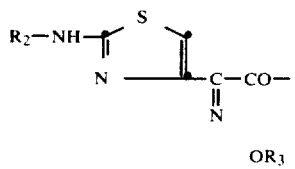

in which R₃ is defined according to claim 1 and R₂ is a t-butoxycarbonyl, 2,2,2-trichloroethoxycarbonyl, trichloroacetyl, chloroacetyl, trityl, dibenzyl, benzyl, benzyloxycarbonyl, p-nitrobenzyloxycarbonyl, p-methoxybenzyloxycarbonyl, formyl or trifluoroacetyl group.

3. A new product according to claim 1, in which R₄ represents a radical of the general formula:

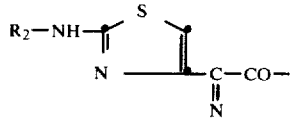

in which R₂ is defined as in claim 1 and R₃ is a trityl, tetrahydropyranyl or 2-methoxyprop-2-yl protective group of the oxime group.

4. A new product according to claim 1, in which R₄ is a radical of the general formula:

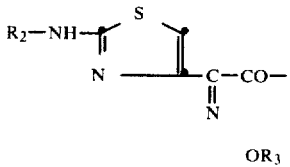

in which R₂ is defined as in claim 1 and R₃ is a carboxyalkyl group represented by the general formula:

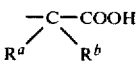

in which $R^a$ and $R^b$ are defined as in claim 1 protected beforehand by a radical chosen from amongst methoxymethyl, t-butyl, benzhydryl, benzyl, nitrobenzyl and p-methoxybenzyl.

5. A new product according to claim 1, in which R₁ is chosen from amongst methoxymethyl, t-butyl, benzhydryl, benzyl, nitrobenzyl and p-methoxybenzyl radicals.

6. 2-Benzhydryloxycarbonyl-8-oxo-3-(2-oxoethyl)-7-tritylamino-5-oxa-1-azabicyclo[4.2.0]oct-2-ene.

7. The syn isomer of 2-benzhydryloxycarbonyl-7-[2-methoxyimino-2-(2-tritylaminothiazol-4-yl)-acetamido]-8-oxo-3-(2-oxoethyl)-5-oxa-1-azabicyclo[4.2.0]oct-2-ene.

8. 2-Benzhydryloxycarbonyl-7-t-butoxycarbonylamino-3-(2-oxoethyl)-8-oxo-5-oxa-1-azabicyclo[4.2.0]oct-2-ene.

9. 2-Benzhydryloxycarbonyl-3-(2-oxoethyl)-8-oxo-7-phenylacetamido-5-oxa-1-azabicyclo[4.2.0]oct-2-ene.

10. 2-Benzhydryloxycarbonyl-3-(2-oxoethyl)-8-oxo-7-phenoxyacetamido-5-oxa-1-azabicyclo[4.2.0]oct-2-ene.

11. 2-Benzhydryloxycarbonyl-7α-methoxy-3-(2-oxoethyl)-8-oxo-7-phenoxyacetamido-5-oxa-1-azabicyclo[4.2.0]oct-2-ene.

12. 2-p-Nitrobenzyloxycarbonyl-3-(2-oxoethyl)-8-oxo-7-tritylamino-5-oxa-1-azabicyclo[4.2.0]oct-2-ene.

* * * * *